(12) United States Patent
Verser et al.

(10) Patent No.: US 8,329,436 B2
(45) Date of Patent: Dec. 11, 2012

(54) METHOD OF MAKING PROPANOL AND ETHANOL FROM PLANT MATERIAL BY BIOLOGICAL CONVERSION AND GASIFICATION

(75) Inventors: Dan W. Verser, Menlo Park, CA (US); Timothy J. Eggeman, Lakewood, CO (US)

(73) Assignee: Zeachem, Inc., Menlo Park, CA (US)

( * ) Notice: Subject to any disclaimer, the term of this patent is extended or adjusted under 35 U.S.C. 154(b) by 1310 days.

(21) Appl. No.: 12/029,321

(22) Filed: Feb. 11, 2008

(65) Prior Publication Data

US 2008/0193989 A1   Aug. 14, 2008

Related U.S. Application Data

(60) Provisional application No. 60/889,165, filed on Feb. 9, 2007.

(51) Int. Cl.
| | |
|---|---|
| C12P 7/10 | (2006.01) |
| C12P 7/06 | (2006.01) |
| C12P 7/04 | (2006.01) |
| C12P 7/52 | (2006.01) |
| C12P 7/54 | (2006.01) |
| C12P 1/04 | (2006.01) |

(52) U.S. Cl. ........ 435/165; 435/161; 435/157; 435/141; 435/140; 435/170

(58) Field of Classification Search .................. 435/165, 435/161, 157, 170, 141, 140
See application file for complete search history.

(56) References Cited

U.S. PATENT DOCUMENTS

| | | | |
|---|---|---|---|
| 1,421,605 | A | 7/1922 | Steffens |
| 2,079,414 | A | 5/1937 | Lazier |
| 2,565,487 | A | 12/1948 | Filachione et al. |
| 2,782,243 | A | 2/1957 | Hess et al. |
| 3,769,329 | A | 10/1973 | Paulik et al. |
| 4,055,590 | A | 10/1977 | Gruber et al. |
| 4,100,189 | A | 7/1978 | Mercier |

(Continued)

FOREIGN PATENT DOCUMENTS

GB         933714         8/1963

(Continued)

OTHER PUBLICATIONS

Agreda, V.H. et al. "High Purity Methyl Acetate Via Reactive Distillation", Chemical Engineering Progress, p. 40-46, Feb. 1990.

(Continued)

*Primary Examiner* — Rosanne Kosson
(74) *Attorney, Agent, or Firm* — Sheridan Ross PC

(57) ABSTRACT

The invention relates to processes that efficiently convert carbon-containing materials, such as biomass, into products in such a manner that the energy, carbon, and mass content of the materials are efficiently transferred into such products. Such methods include converting the materials into at least one intermediate by a biological conversion process and at least one intermediate by a thermochemical conversion process and reacting the intermediates to form the product. Such methods have a chemical energy efficiency to produce the product that is greater than the chemical energy efficiency of a solely biological conversion process to produce the product and that is greater than the chemical energy efficiency of a process in which all of the material is initially subjected to a thermochemical conversion step as part of the process to produce the product.

39 Claims, 4 Drawing Sheets

U.S. PATENT DOCUMENTS

| | | |
|---|---|---|
| 4,113,662 A | 9/1978 | Wall |
| 4,206,036 A | 6/1980 | Takeuchi et al. |
| 4,275,234 A | 6/1981 | Baniel et al. |
| 4,282,323 A | 8/1981 | Yates |
| 4,359,404 A | 11/1982 | Grey et al. |
| 4,370,507 A | 1/1983 | Hargis et al. |
| 4,371,619 A | 2/1983 | Schwartz et al. |
| 4,379,028 A | 4/1983 | Berg et al. |
| 4,405,717 A | 9/1983 | Urbas |
| 4,407,954 A * | 10/1983 | Clyde .................... 435/161 |
| 4,421,939 A | 12/1983 | Kiff et al. |
| 4,431,838 A | 2/1984 | Feldman et al. |
| 4,435,595 A | 3/1984 | Agreda et al. |
| 4,444,881 A | 4/1984 | Urbas |
| 4,454,358 A | 6/1984 | Kummer et al. |
| 4,497,967 A | 2/1985 | Wan |
| 4,506,012 A | 3/1985 | Reed |
| 4,568,644 A | 2/1986 | Wang et al. |
| 4,649,112 A | 3/1987 | Datta et al. |
| 4,687,668 A | 8/1987 | Ghommidh et al. |
| 4,698,303 A | 10/1987 | Bailey et al. |
| 4,771,001 A | 9/1988 | Bailey et al. |
| 4,808,526 A | 2/1989 | Lawford |
| 4,851,344 A | 7/1989 | Simon et al. |
| 4,935,360 A | 6/1990 | Klemps et al. |
| 4,939,294 A | 7/1990 | Agreda et al. |
| 5,071,754 A | 12/1991 | Walkup et al. |
| 5,137,818 A | 8/1992 | Harder et al. |
| 5,173,429 A | 12/1992 | Gaddy et al. |
| 5,182,199 A | 1/1993 | Hartley |
| 5,210,296 A | 5/1993 | Cockrem et al. |
| 5,231,017 A | 7/1993 | Lantero et al. |
| 5,412,126 A | 5/1995 | King et al. |
| 5,424,202 A | 6/1995 | Ingram et al. |
| 5,453,365 A | 9/1995 | Sterzel et al. |
| 5,510,526 A | 4/1996 | Baniel et al. |
| 5,563,069 A | 10/1996 | Yang |
| 5,599,976 A | 2/1997 | Scates et al. |
| 5,620,877 A | 4/1997 | Farone et al. |
| 5,693,296 A | 12/1997 | Holtzapple et al. |
| 5,723,639 A | 3/1998 | Datta et al. |
| 5,750,732 A | 5/1998 | Verser et al. |
| 5,753,474 A | 5/1998 | Ramey et al. |
| 5,766,439 A | 6/1998 | Eyal et al. |
| 5,773,653 A | 6/1998 | Baniel |
| 5,780,276 A | 7/1998 | Baniel |
| 5,865,898 A | 2/1999 | Holtzapple et al. |
| 5,874,263 A | 2/1999 | Holtzapple et al. |
| 5,986,133 A | 11/1999 | Holtzapple et al. |
| 6,043,392 A | 3/2000 | Holtzapple et al. |
| 6,136,577 A | 10/2000 | Gaddy |
| 6,160,173 A | 12/2000 | Eyal et al. |
| 6,262,313 B1 | 7/2001 | Holtzapple et al. |
| 6,284,904 B1 | 9/2001 | Ponnampalam |
| 6,368,819 B1 | 4/2002 | Gaddy et al. |
| 6,395,926 B1 | 5/2002 | Holtzapple et al. |
| 6,478,965 B1 | 11/2002 | Holtzapple et al. |
| 6,509,180 B1 | 1/2003 | Verser et al. |
| 6,740,508 B2 | 5/2004 | Ulrich et al. |
| 6,852,517 B1 | 2/2005 | Suthers et al. |
| 6,926,810 B2 | 8/2005 | Cockrem et al. |
| 6,927,048 B2 | 8/2005 | Verser et al. |
| 7,074,603 B2 | 7/2006 | Verser et al. |
| 7,309,602 B2 | 12/2007 | David |
| 7,351,559 B2 | 4/2008 | Verser et al. |
| 7,507,562 B2 | 3/2009 | Verser et al. |
| 7,601,865 B2 | 10/2009 | Verser et al. |
| 7,682,812 B2 | 3/2010 | Verser et al. |
| 2005/0112739 A1 | 5/2005 | Golubkov |
| 2006/0024801 A1 | 2/2006 | Holtzapple et al. |
| 2006/0222585 A1 | 10/2006 | Verser et al. |
| 2007/0014895 A1 | 1/2007 | Holtzapple et al. |
| 2008/0102502 A1 | 5/2008 | Foody et al. |
| 2008/0176301 A1 | 7/2008 | Granda et al. |
| 2008/0248540 A1 | 10/2008 | Yang |
| 2008/0280338 A1 | 11/2008 | Hall et al. |
| 2009/0081749 A1 | 3/2009 | Verser et al. |
| 2009/0203098 A1 | 8/2009 | Verser |
| 2009/0281354 A1 | 11/2009 | Mariansky et al. |
| 2010/0120104 A1 | 5/2010 | Reed |

FOREIGN PATENT DOCUMENTS

| | | |
|---|---|---|
| JP | S59-29633 | 2/1984 |
| JP | 11-503514 | 3/1999 |
| WO | WO 83/03409 | 10/1983 |
| WO | WO 93/00440 | 1/1993 |
| WO | WO 99/00352 | 1/1999 |
| WO | WO 99/00512 | 1/1999 |
| WO | WO0053791 | 9/2000 |
| WO | WO2005073161 | 8/2005 |
| WO | WO 2006/007406 | 1/2006 |
| WO | WO 2007/009085 | 1/2007 |
| WO | WO 2008/070561 | 6/2008 |

OTHER PUBLICATIONS

Buschhorn, H., et al., "Production and utilization of ethanol by the homoacetogen *Acetobacterium woodii*," Appl. Environ. Microbiol. 55, 1835-1840 (1989).

Gallagher, et al., "Energy Production with Biomass: What are the Prospects", Choices, 21(1): 21-25 (2006).

Tang, I.C., et al., "Acetic Acid Production from Whey Lactose by the Co-culture of *Streptococcus lactis* and *Clostridium formicoaceticum*", Applied Microbiology and Biotechnology, vol. 28, p. 138-143 (1988).

Wang, D.I., et al., "A Novel Route to the Production of Acetic Acid by Fermentation", AIChE Symposium Series-Biochemical Engineering: Renewable Sources, No. 181, vol. 74, p. 105-110 (1978).

Xu, Z.P, et al., "Kinetics of Acetic Acid Esterification over Ion Exchange Catalysts", Can. J. Chem. Eng., pp. 493-500, vol. 74 (1996).

Yang, S.T., et al., "Kinetics and Mathematical Modeling of Homoacetic Fermentation of Lactate by *Clostridium formicoaceticum*", Biotechnology and Bioengineering, vol. 32, p. 797-802 (1988).

Drake, "Acetogenesis, Acetogenic Bacteria, and the Acetyl-CoA 'Wood/Ljungdahl' Pathway: Past and Current Perspectives", Acetogenesis, 1994, Chapter 1, pp. 3-60, Chapman and Hall, Inc., New York, NY.

Roels, "Energetics and kinetics in biotechnology", 1983, pp. 41-42, Elsevier Biomedical Press.

International Search Report for International (PCT) Patent Application No. PCT/US08/53611, mailed Sep. 16, 2008.

Written Opinion for International (PCT) Patent Application No. PCT/US08/53611, mailed Sep. 16, 2008.

Drake, Acetogenesis, Figure 12.2, 1994, p. 343, Chapman Hall, New York.

Ben-Bassat et al., "Ethanol production by thermophilic bacteria: metabolic control of end product formation in *Thermoanaerobium brockii*", J Bacteriol Apr. 1981, 146:1, p. 192-9 (Abstract only).

Borden, J.R., Lee, Y.Y., Yoon, H.H., "Simultaneous Saccharification and Fermentation of Cellulosic Biomass to Acetic Acid", Appl Biochem and Biotech, vol. 84-86, p. 963-970, 2000.

Brownell, J., Nakas, J., "Bioconversion of Acid-Hydrolyzed Poplar Hemicellulose to Acetic Acid by *Clostridium thermoaceticum*", J. Ind. Microbiol, vol. 7, p. 1-6, 1991.

Busche et al., Biotechnol. Bioeng. Symp., "Recovery of Acetic Acid From Dilute Acetate Solution", No. 12, pp. 249-262 (1982).

Busche, Robert M., Recovering Chemical Products from Dilute Fermentation Broths, Biotechnology and Bioengineering Symp. No. 13, 597-615 (1983).

Chang, V.S., Holtzapple, M.T., "Fundamental Factors Affecting Biomass Enzymatic Reactivity", Appl. Biochem. and Biotech.; vol. 84-86, p. 5-37, 2000.

Cooper et al. "A Renewed Boost for Ethanol", Chemical Engineering, Feb. 1999, p. 35-39.

Drake, et al, "Old Acetogens, New Light" Ann. NY Acad. Sci. 1125: 100-128 (2008).

Eggeman et al. "Recovery of Organic Acids from Fermentation Broths", Mar. 1, 2005, Applied Biochemistry and Biotechnology, vol. 122, pp. 605-618.

Eggeman Tim et al: "The importance of utility systems in today's biorefineries and a vision for tomorrow" Applied Biochemistry and Biotechnology, vol. 130, No. 1-3, Mar. 2006, pp. 361-381, XP002499935 ISSN: 0273-2289.

Filachione et al., Preparation of Esters by Reaction of Ammonium Salts with Alcohols, 5265-5267 (Nov. 1951) [Presented in part at the 116th A.C.S. Meeting held in Atlantic City, N.J., Sep. 1949, and also at the Miniature meeting of the Philadelphia Section of the American Chemical Society held in Philadelphia, PA., in Jan. 1949.].

Grohmann et al., Process Biochem., "Saccharification of Corn Fibre by Combined Treatment with Dilute Sulphuric Acid and Enzymes", vol. 32, No. 5, pp. 405-415 (1997).

Gulati et al. "Assessment of Ethanol Production Options for Corn Products", Bioresource Technology 58, 1996, p. 253-264.

Husson et al., Regeneration of Lactic and Succinic Acid-Laden Basic Sorbents by Leaching with a Volatile Base in an Organic Solvent, Ind. Eng. Chem. Res. 37:2996-3005 (1998).

Leathers et al., "Saccharification of Corn Fiber Using Enzymes from *Aureobasidium* sp. Strain NRRL Y-2311-1", Applied Biochemistry and Biotechnology, vol. 59, 1996, p. 337-347.

Luo et al., "Kinetics of Simultaneous Saccharification and Lactic Acid Fermentation Processes", Biotechnol. Prog. 1997, 13, 762-767.

Matar et al. "Chemistry of Petrochemical Processes", Gulf Publishing Company, 1994, cover, contents, p. 162-163.

Miller, Richard W. et al: "Extraction of Lactic Acid from a Calcium Lactate Solution Using Amine-Containing Solvents and Carbon Dioxide Gas. 1. Experimental Procedures" Industrial & Engineering Chemistry Research, 35(4), 1156-62, 1996.

Othmer, "Acetic Acid Recovery Methods", Chemical Engineering Progress, Jul. 1958, pp. 48-59, vol. 54, No. 7.

Pöpken, et al., "Reaction Kinetics and Chemical Equilibrium of Homogeneously and Heterogeneously Catalyzed Acetic Acid Esterification with Methanol and Methyl Acetate Hydrolysis", Industrial and Engineering Chemistry Research, Jun. 17, 2000, pp. 2601-2611, vol. 39, No. 7.

Reisinger et al., Extraction and Sorption of Acetic Acid at pH above pKa to Form Calcium Magnesium Acetate, Ind. Eng. Chem. Res., 34:845-852 (1995).

Richert et al., "Thermophilic Fermentation to Make Ethanol from Carbohydrate Byproducts", Genetic Engineering News, Oct. 1, 1998, 1 page.

Ricker et al., Solvent Extraction With Amines for Recovery of Acetic Acid From Dilute Aqueous Industrial Streams, J. Separ. Proc. Technol., 1(2):23-30 (1980).

Ricker, et al., "Solvent Properties of Organic Bases for Extraction of Acetic Acid from Water", Journal of Separation Process Technology, 1979, pp. 36-41, vol. 1, No. 1.

Saha, et al., "Recovery of dilute acetic acid through esterification in a reactive distillation column", Catalysis Today, 2000, pp. 147-157, vol. 60.

Schoberth et al., "Considerations on the Energy Metabolism of *Clostridium kluyveri*" Arch. Mikrobiol. 65, 318-328 (1969).

Schwartz, et al., "Acetic Acid Production by *Clostridium thermoaceticum* in pH-Controlled Batch Fermentations at Acidic pH", Applied and Environmental Microbiology, Jun. 1982, pp. 1385-1392, vol. 43, No. 6.

Tamada et al., Extraction of Carboxylic Acids with Amine Extractants. 3. Effect of Temperature, Water Coextraction, and Process Considerations, Ind. Eng. Chem. Res. 29:1333-1338 (1990).

Wardell et al., Solvent Equilibria for Extraction of Carboxylic Acids from Water, Journal of Chemical and Engineering Data, 23(2):144-148 (1978).

Xin et al. "Recovery of acetic acid from waste water", Chemical Engineering (China), vol. 24, No. 5, pp. 41-44 (including translated abstract), Abstract only, 1996.

Zeikus et al., "Thermophilic Ethanol Fermentations", Basic Life Sci, 1981, vol. 18, p. 441-61 (Abstract only).

Zhicai et al., Esterification—Distillation of Butanol and Acetic Acid, Chemical Engineering Science, 53(11):2081-2088 (1998).

International Preliminary Report on Patentability for International (PCT) Patent Application No. PCT/US08/53611, mailed Aug. 20, 2009.

\* cited by examiner

METHOD OF MAKING PROPANOL AND ETHANOL FROM PLANT MATERIAL BY BIOLOGICAL CONVERSION AND GASIFICATION

CROSS REFERENCE TO RELATED APPLICATION

This application claims priority under 35 U.S.C. §119(e) to U.S. Provisional Patent Application Ser. No. 60/889,165 entitled "HIGH ENERGY YIELD CONVERSION PROCESS FOR PRODUCING FUELS FROM RENEWABLE RESOURCES" filed Feb. 9, 2007, which is incorporated herein in its entirety by this reference.

FIELD OF THE INVENTION

The invention relates to processes that efficiently convert carbon-containing materials, such as biomass, into products in such a manner that the energy, carbon, and mass content of the materials are efficiently transferred into such products.

BACKGROUND OF THE INVENTION

It is desirable to produce products, including liquid fuels such as ethanol, from renewable resources, e.g., biomass, because of the limited supply of easily recovered petroleum and natural gas and the increasing price of recovery. In addition, the use of products produced from biomass will reduce the buildup of carbon dioxide in the atmosphere.

It is particularly desirable to produce products from biomass in such a manner that a maximal amount of the energy content, carbon content and mass content contained within such materials is transferred to such products. Current processes that use biomass, however, are not efficient in such transfer.

Traditional renewable-based chemicals, such as ethanol and lactic acid, have been produced from agricultural grains. For example, sugars can easily be produced from the starches of corn, wheat or other grains by enzymes or acid hydrolysis or be recovered from sugar-containing crops such as sugar cane at high yield. Such sugars can then be easily converted to ethanol by, for example, natural yeast organism fermentation. Although for yeast fermentation about 96% of the energy in the sugar material is transferred into ethanol, only about 67% of the carbon in the sugar material is transferred into ethanol. This low carbon efficiency is due to yeast producing two moles of carbon dioxide for each two moles of ethanol produced from one mole of glucose. This process results in a maximum mass (or dry weight) yield of about 52%.

However, the conversion of biomass into ethanol is not as efficient as the conversion of sugars into ethanol. Biomass is a complex material, containing not only starch and other sugars but also structural parts (e.g., stems, leaves, cobs, etc.) that are complex and contain several components, including cellulose, hemicellulose, and lignin. For example, about 45% of a corn plant is the grain (corn kernel) and the structural parts make up the remaining about 55%. Each of these components comprises about 70% carbohydrate. As such, the starch fraction of the kernel of corn, one of the most productive grains, is only about 32% (45%×70%) of the entire plant's mass and energy content.

Biomass is a heterogeneous mixture, the components of which are intermingled and cannot be separated by simple physical means. Typically, biomass includes two main fractions: carbohydrates and non-carbohydrates. The carbohydrate fraction includes cellulose, hemicellulose, starch and sugars. Cellulose, hemicellulose and starch typically include sugars such as glucose, xylose, arabinose, mannose, etc. The non-carbohydrate fraction includes lignin, which is a complex phenolic material, as well as proteins, resinous materials and minerals. The carbohydrate fraction of a typical biomass, such as wood, may comprise about 60% to about 70% of the total material on a dry weight basis, while lignin and other non-carbohydrates comprise the remainder. Other forms of biomass, however, may have a quite low proportion of carbohydrates. For example residues from the forestry industry may include bark, which may be quite low in carbohydrate (often less than about 25% of the total material on a dry weight basis).

A corn plant is one of the most efficient examples of biomass used to produce ethanol. However, since a corn-based process converts only the starch fraction of the corn plant into ethanol and since starch is only about 32% of the plant's mass and energy content (as described above), the energy yield from the whole corn plant is only about 31% (i.e., 32%×96%), and the dry weight yield is only about 17% (i.e., 32%×52%). Such yields represent an important limitation on the use of grain crops for conversion to renewable-based fuels and chemicals.

In order to overcome this limitation, and to avoid competition for grain as an important human and animal food source, there have been many efforts to produce renewable chemicals and fuels from complex cellulosic biomass, especially the non-grain parts of crops as well as non-food plants such as woody plants and grasses. The structural (non-edible) parts of a food plant (e.g., the stover from corn plants or the straw from wheat plants) can comprise up to about 70% carbohydrate for corn on a dry weight basis, in the form of cellulose and hemicellulose. If one could efficiently process all of the carbohydrate fractions of the plant structure using a direct yeast-based ethanol fermentation, for example, one could convert up to about 67% (70%×96%) of the energy stored in the plant structure to ethanol. However, only about 36% (70%×52%) of the dry weight could be converted to ethanol.

Woody plants and grasses have high yields of total biomass per unit of land area and thus can provide an attractive economic basis if one can utilize them efficiently. In addition it has been found that even for certain food crops, such as sugar cane and corn, the overall biomass yield can be improved by changing the plant breeding criteria away from traditional targets, such as sucrose concentration and kernel yield, to total energy yield per acre of planted land.

The conversion of cellulosic biomass to ethanol has been a very active field of research because of the availability of structural biomass and potential higher yield of ethanol compared to using only grains. There are, however, a number of unresolved technical problems that need to be solved before this approach can provide a significant source of renewable based fuels and chemicals.

One method to convert biomass to ethanol is a direct analogy to the traditional ethanol fermentation process, based on the yeast fermentation of sugars from starch derived from, for example, corn and wheat. However, the sugars in this case are derived from the hemicellulose and cellulose fractions of biomass.

There has been research on extracting sugars from biomass for many years, and a number of methods have been developed. One method is acid hydrolysis of the carbohydrate fractions. Since the main components of the carbohydrate fraction of biomass are sugar polymers, they can be hydrolyzed using an acid catalyst in water. Many different mineral and organic acids, and a wide range of conditions, have been attempted. One concern with acid hydrolysis is the reaction of the product sugars with acid to produce degradation byproducts that reduce sugar yield and may inhibit fermentation.

An alternative process is the use of enzymes to hydrolyze the carbohydrates. Various hemicellulase and cellulase enzymes have been found in nature and developed as catalysts for the breakdown of biomass. In addition, it is often preferred to pretreat the biomass to separate the lignin and hemicellulose from the cellulose before hydrolysis. Many different combinations of pretreatment and hydrolysis have been developed.

Biomass, in contrast to starch, contains a number of different kinds of sugars. Cellulose is largely a glucose polymer, but hemicellulose is a very complex amorphous and branched polymer that usually contains several different sugars. A major component of hemicellulose contains xylose and arabinose, so-called C5 sugars. Each type of biomass contains a different mix of hemicellulose sugars.

The natural yeasts used for ethanol fermentation only ferment sugars such as glucose, sucrose or other so-called C6 sugars. They typically do not ferment the C5 sugar xylose (found in hemicellulose) to ethanol. Thus, research continues to be conducted to find an efficient way to convert the mixed sugars derived from biomass to ethanol.

Even if these technical issues are resolved, however, there is still the limitation that only part of the biomass (i.e., the carbohydrate fraction) can be converted by direct fermentation to products. And because of the limitation of the direct biological approach, there remains a significant yield loss.

The non-carbohydrate fraction of biomass contains many non-fermentable components such as lignin. Some of these components may also be inhibitory to the ethanol-producing organism. Lignin is often burned to offset energy use in the fermentation and recovery process or sold as excess power or heat energy. For example, many sugar cane mills burn left over plant structural material or bagasse.

An alternative to fermentation of the carbohydrates in biomass to ethanol is the conversion of all of the biomass including the carbohydrates and lignin by thermochemical means, such as gasification, to an intermediate syngas. Syngas is comprised of carbon monoxide (CO), carbon dioxide ($CO_2$), and hydrogen ($H_2$) as well as other minor components such as tars and sulfur compounds.

There are a variety of gasification processes to produce syngas, each of which typically cracks carbon-containing materials to produce a gaseous mixture containing CO, $CO_2$ and $H_2$, along with tars and particulates from the mineral fraction of the raw material. A second reactant, such as steam, air, or oxygen, can be added to the process. Alternatively, gasification can be conducted in the absence of such reactants; this process is often called pyrolysis. The product syngas usually must be filtered and then adjusted in composition depending upon the use. In addition to filtration, the syngas may be cleaned up, for example to remove tars by various means, such as scrubbing or reaction, and to remove specific impurities, such as sulfur compounds. The composition of the syngas can be adjusted by various chemical means or by separation of certain components. Hydrogen content can be adjusted by the water-gas shift reaction between carbon monoxide and steam to give hydrogen and carbon dioxide. Pressure swing absorption can be used, for example, to separate and purify hydrogen from syngas.

The thermochemical conversion of biomass materials to syngas results in a decrease in energy of the products along with the production of byproduct heat. About 70% of the energy content of biomass is converted into syngas by gasification.

After the conversion of all of the components of biomass to syngas, two options have been proposed for the conversion of the syngas to ethanol or other products. One approach is the conversion of the syngas by a fermentation process. There are a number of organisms that can utilize syngas to produce products, such as ethanol. These fermentations are less able to conserve energy than are sugar fermentations, typically being about 80% efficient in converting the energy in the syngas into product chemical energy. Thus the overall transfer of biomass energy to ethanol by such a combined gasification and fermentation process is about 56% (70%×80%).

A second approach is the use of a catalytic chemical process to convert syngas to products such as ethanol. This process requires a catalyst as well as high temperature and pressure. The catalytic chemical process has the same overall chemistry and thermal efficiency as the gasification plus fermentation process, i.e., 56%, since the overall chemistry is the same.

An advantage of the thermochemical route to produce, for example, ethanol is that it can potentially convert more of the fractions of the plant into products because it can convert the lignin fraction. On the other hand, this route suffers from a theoretical yield loss in each step, so overall its energy efficiency is limited. The thermochemical process wastes the energy stored in the carbohydrate fraction of the biomass by degrading the carbohydrates to syngas, which is less efficient than a biological conversion of the carbohydrates to a desired product.

For each of these described processes, there is also a limit on what product can be produced efficiently. Direct fermentation of biomass to a desired product is limited by the biochemical pathways that can be discovered or engineered into an organism as well as by the need to maintain the viability of the organism and to use available substrates. Thermochemical processing of biomass also has limitations because, for example, fermentation of syngas is also limited by organism constraints, whereas chemical catalysts are limited by their ability to convert syngas selectively to a desired product rather than to a complex mixture.

Thus, there remains a need to produce products from biomass such that energy, carbon and mass contained in all parts of the biomass are efficiently transferred to the products. It would be desirable to have a process that maximizes the use of both the carbohydrate and non-carbohydrate fractions of biomass to produce a product.

SUMMARY OF THE INVENTION

One embodiment of the present invention is a method for producing a product from a material comprising carbon-containing compounds, wherein less than about 75% by weight of the carbon-containing compounds are carbohydrate substances. The method includes converting the material into at least two intermediates, wherein at least one intermediate is produced by a biological conversion process and at least one intermediate is produced by a thermochemical conversion process. The method further includes reacting at least one biological process-produced intermediate and at least one thermochemical process-produced intermediate to form the product. In this process, the chemical energy efficiency of the method to produce the product from the material is greater than the chemical energy efficiency of a solely biological conversion process to produce the product and is greater than the chemical energy efficiency of a process in which all of the material is initially subjected to a thermochemical conversion step as part of the process to produce the product. In some embodiments, the chemical energy efficiency of the method is at least about 60%, 65%, 70%, 75%, 80%, or 82%. In some embodiments, greater than about 70% of carbohydrate substances in the material is converted into the product or at least about 70%, 75%, 80%, 90%, 95% or about 100% of carbohydrate substances in the material is converted into the product. In other embodiments, essentially no carbon dioxide is produced in the biological conversion process or only one mole of carbon dioxide is produced per mole of monosaccharide or monosaccharide unit in the material.

In various embodiments, the material includes carbohydrate substances and non-carbohydrate substances. The material can also comprise biomass and can be selected from herbaceous matter, agricultural residue, forestry residue, municipal solid waste, waste paper, pulp and paper mill residue. The material can also be selected from the group consisting of trees, shrubs, grasses, wheat, wheat straw, wheat midlings, sugar cane bagasse, corn, corn husks, corn kernel, corn fiber, municipal solid waste, waste paper, yard waste, branches, bushes, energy crops, fruits, fruit peels, flowers, grains, herbaceous crops, leaves, bark, needles, logs, roots, saplings, short rotation woody crops, switch grasses, vegetables, vines, sugar beet pulp, oat hulls, hard woods, wood chips, intermediate streams from pulping operations and soft woods, and in a preferred embodiment, is selected from the group consisting of trees, grasses, whole plants, and structural components of plants.

The biological conversion process can comprise fermentation or comprise culturing at least one microorganism. Such a microorganism can be at least one homofermentative microorganism, and can be selected from homoacetogenic microorganisms, homolactic microorganisms, propionic acid bacteria, butyric acid bacteria, succinic acid bacteria and 3-hydroxypropionic acid bacteria. In other embodiments, the microorganism is of a genus selected from *Clostridium, Lactobacillus, Moorella, Thermoanaerobacter, Propionibacterium, Propionispera, Anaerobiospirillum,* and *Bacteriodes*. In other embodiments, the microorganism is of a species selected from *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*.

In some embodiments, the at least one biological process-produced intermediate can comprise a carboxylic acid, a salt thereof, or a mixture thereof. More specifically, the at least one biological process-produced intermediate can be selected from acetic acid, lactic acid, propionic acid, butyric acid, succinic acid, 3-hydroxypropionic acid, a salt of any of the acids, and a mixture of any of the acids and respective salts. Alternatively, the at least one biological process-produced intermediate can be selected from acetic acid, an acetate salt, a mixture of acetic acid and acetate salt, lactic acid, a lactate salt, a mixture of lactic acid and lactate salt, propionic acid, a propionate salt, a mixture of propionic acid and propionate salt, butyric acid, a butyrate salt, a mixture of butyric acid and butyrate salt, succinic acid, a succinate salt, a mixture of succinic acid and succinate salt, 3-hydroxypropionic acid, a 3-hydroxypropionate salt, and a mixture of 3-hydroxypropionic acid and 3-hydroxypropionate salt.

The thermochemical conversion process can be selected from gasification, pyrolysis, reforming, and partial oxidation. The at least one thermochemical process-produced intermediate can be selected from syngas, a component of syngas, a mixture of syngas components, pyrolysis gas, a component of pyrolysis gas, and a mixture of pyrolysis gas components. In other embodiments, the at least one thermochemical process-produced intermediate can be selected from hydrogen, carbon monoxide, carbon dioxide, and methanol.

In a further embodiment, the at least one biological process-produced intermediate comprises a salt of a carboxylic acid, and the method further comprises acidifying the salt of the carboxylic acid to form the carboxylic acid prior to the step of reacting. This embodiment can also include esterifying the carboxylic acid prior to the step of reacting. In this embodiment, the step of acidifying can include introducing carbon dioxide or an acid with a lower pKa than the carboxylic acid being acidified to a solution comprising the salt of the carboxylic acid. Alternatively, the step of acidifying can include introducing a tertiary amine with carbon dioxide to form an acid/amine complex. This embodiment can further include contacting the acid/amine complex with a water immiscible solvent to form an ester of the water immiscible solvent and the carboxylic acid.

In various embodiments, the step of reacting the at least one biological process-produced intermediate and the at least one thermochemical process-produced intermediate to produce the product can be selected from chemical conversion and biological conversion. In some embodiments, the step of reacting the at least one biological process-produced intermediate and the at least one thermochemical process-produced intermediate is a process of reduction to produce the product or can be selected from hydrogenation, hydrogenolysis and reduction by carbon monoxide.

The product of the present invention can be selected from an alcohol, a carboxylic acid, a salt of a carboxylic acid, and an ester of a carboxylic acid or can be selected from a monohydric alcohol and a dihydric alcohol. In specific embodiments, the product can be selected from ethanol, propanol, propylene glycol, butanol, 1,4-butanediol, 1,3-propanediol, or methyl esters thereof.

In one embodiment, the method of the present invention can include fractionating the material to form a carbohydrate-containing fraction for conversion to an intermediate by a biological conversion process, and to form a residue fraction comprising lignin for conversion to an intermediate by a thermochemical conversion process. In this embodiment, the step of fractionating can be selected from physical treatment, metal ion treatment, ultraviolet light treatment, ozone treatment, oxygen treatment, organosolv treatment, steam explosion treatment, lime impregnation with steam explosion treatment, lime impregnation without steam treatment, hydrogen peroxide treatment, hydrogen peroxide/ozone (peroxone) treatment, acid treatment, dilute acid treatment, and base treatment.

In one embodiment of the present invention, the at least one biological process-produced intermediate is produced by fermentation of carbohydrate substances in the material, and the at least one thermochemical process-produced intermediate is produced by thermochemical conversion of non-carbohydrate substances in the material. In this embodiment, the at least one biological process-produced intermediate and the at least one thermochemical process-produced intermediate are chemically reacted to produce the product.

In another embodiment of the present invention, a portion of at least one biological process-produced intermediate is produced by fermentation of carbohydrate substances in the material, the at least one thermochemical process-produced intermediate is produced by thermochemical conversion of non-carbohydrate substances in the material, and a portion of at least one biological process-produced intermediate is produced by fermentation of at least a portion of the at least one thermochemical process-produced intermediate. In this embodiment, the two biological process-produced intermediates and at least a portion of the remaining at least one thermochemical process-produced intermediate are chemically reacted to produce the product.

In a further embodiment of the present invention, the material is fermented to produce at least one biological process-produced intermediate and a fermentation residue comprising non-fermented components of the material. In this embodiment, the at least one thermochemical process-produced intermediate is produced by thermochemical conversion of the fermentation residue, and the at least one biological process-produced intermediate and the at least one thermochemical process-produced intermediate are chemically reacted to produce the product.

A particular embodiment of the present invention is a method for producing ethanol from a material comprising carbon-containing compounds, wherein less than about 75% by weight of the carbon-containing compounds are carbohydrate substances. The method includes, converting the material into at least two intermediates, wherein at least one intermediate is produced by a biological conversion process and comprises acetic acid, an acetate salt, an acetate ester or a mixture of acetic acid, acetate ester and an acetate salt, and wherein at least one intermediate is produced by a thermochemical conversion process and comprises a reductant. The method further includes chemically reacting the reductant and the acetic acid, acetate salt, acetate ester or mixture of acetic acid, acetate ester and acetate salt to produce ethanol. In this method, the chemical energy efficiency of the method is greater than the chemical energy efficiency of a solely biological conversion process to produce ethanol and is greater than the chemical energy efficiency of a process in which all of the material is initially subjected to a thermochemical conversion step as part of the process to produce ethanol. In this embodiment, the reductant can be selected from hydrogen, carbon monoxide, and a mixture of hydrogen and carbon monoxide. In this embodiment, the step of converting can include producing the acetic acid, acetate salt, acetate ester or mixture of acetic acid, acetate ester and acetate salt by a biological conversion process of carbohydrate substances in the material, and producing the reductant by a thermochemical conversion of non-carbohydrate substances in the material. In this embodiment, the biological conversion process can include fermentation.

Another particular embodiment of the present invention is a method for producing ethanol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises a biological process-produced intermediate selected from acetic acid, an acetate salt, an acetate ester or a mixture of acetic acid, acetate ester and acetate salt, and at least one intermediate is produced by a thermochemical conversion process and comprises hydrogen and carbon monoxide. In this embodiment, the step of converting includes producing a portion of at least one biological process-produced intermediate by biological conversion of carbohydrate substances in the material, and producing a portion of at least one biological process-produced intermediate by biological conversion of carbon monoxide and a portion of the hydrogen produced by the thermochemical conversion process. The method further includes chemically reacting remaining hydrogen produced by the thermochemical conversion process and biological process-produced intermediates to produce ethanol. In this process, the chemical energy efficiency is greater than the chemical energy efficiency of a solely biological conversion process to produce ethanol and is greater than the chemical energy efficiency of a process in which all of the material is initially subjected to a thermochemical conversion step as part of the process to produce ethanol. In this embodiment, the biological conversion processes can comprise fermentation.

In a further embodiment, the present invention is a method for producing ethanol from a material comprising carbon-containing compounds, wherein less than about 75% by weight of the carbon-containing compounds are carbohydrate substances. This embodiment includes converting the material into at least two intermediates, wherein at least one intermediate is produced by a biological conversion process and comprises a biological process-produced intermediate selected from the group consisting of acetic acid, an acetate salt, an acetate ester or a mixture of acetic acid, acetate ester and acetate salt, and at least one intermediate is produced by a thermochemical conversion process and comprises hydrogen and carbon monoxide. In this embodiment, the step of converting comprises producing a portion of at least one biological process-produced intermediate by biological conversion of carbohydrate substances in the material, and producing a portion of at least one biological process-produced intermediate by biological conversion of a portion of the carbon monoxide produced by the thermochemical conversion process. The process further includes chemically reacting hydrogen produced by the thermochemical conversion process and biological process-produced intermediates to form ethanol. In this method, the chemical energy efficiency is greater than the chemical energy efficiency of a solely biological conversion process to produce ethanol and is greater than the chemical energy efficiency of a process in which all of the material is initially subjected to a thermochemical conversion step as part of the process to produce ethanol. In this embodiment, the biological conversion processes can comprise fermentation.

In another embodiment, the present invention is a method for producing ethanol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises a biological process-produced intermediate selected from the group consisting of acetic acid, an acetate salt, an acetate ester or a mixture of acetic acid, acetate ester and an acetate salt, and at least one intermediate is produced by a thermochemical conversion process and comprises hydrogen and carbon monoxide. In this method the step of converting includes producing a portion of at least one biological process-produced intermediate by biological conversion of carbohydrate substances in the material, and producing a portion of at least one biological process-produced intermediate by biological conversion of a portion of the carbon monoxide and a portion of the hydrogen produced by the thermochemical conversion process. The method further includes chemically reacting remaining carbon monoxide produced by the thermochemical conversion process and biological process-produced intermediates to form ethanol. In this method, the chemical energy efficiency is greater than the chemical energy efficiency of a solely biological conversion process and is greater than the chemical energy efficiency of a process in which all of the material is initially subjected to a thermochemical conversion step as part of the process to produce ethanol. In this embodiment, the biological conversion processes can comprise fermentation.

A further embodiment of the present invention is method for producing propylene glycol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises lactic acid, a lactate ester, a lactate salt, or a mixture of lactic acid, lactate ester and a lactate salt, and wherein at least one intermediate is produced by a thermochemical conversion process and comprises a reductant. The method further includes chemically reacting the reductant and the lactic acid, lactate ester, lactate salt, or mixture of lactic acid, lactate ester and lactate salt to produce propylene glycol. In this method, the chemical energy efficiency is greater than the chemical energy efficiency of a solely biological conversion process to produce propylene glycol and is greater than the chemical energy efficiency of a process in which all of the material is initially subjected to a thermochemical conversion step as part of the process to produce propylene glycol. In this method the reductant can be selected from hydrogen, carbon monoxide, and a mixture of hydrogen and carbon monoxide. In addition, the step of converting can include producing the lactic acid, lactate ester, lactate salt, or mixture of lactic acid, lactate ester and lactate salt by a biological conversion process of carbohydrate substances in the material, and producing the reductant by a thermochemical conversion of non-carbohydrate substances in the material. In this method, the biological conversion process can include fermentation.

In a further embodiment, the present invention includes a method for producing propanol and ethanol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises propionic acid, a propionate ester, a propionate salt, acetic acid, an acetate ester, an acetate salt, or a mixture thereof, and wherein at least one intermediate is produced by a thermochemical conversion process and comprises a reductant. The method further includes chemically reacting the reductant and the propionic acid, propionate ester, propionate salt, acetic acid, acetate ester, acetate salt, or a mixture thereof to produce propanol and ethanol. In this method, the chemical energy efficiency is greater than the chemical energy efficiency of a solely biological conversion process to produce propanol and ethanol and is greater than the chemical energy efficiency of a process in which all of the material is initially subjected to a thermochemical conversion step as part of the process to produce propanol and ethanol. In this embodiment, the reductant can be selected from hydrogen, carbon monoxide, and a mixture of hydrogen and carbon monoxide. Further, the step of converting can include producing propionic acid, a propionate ester, a propionate salt, acetic acid, an acetate ester, an acetate salt, or a mixture thereof by a biological conversion process of carbohydrate substances in the material, and producing the reductant by a thermochemical conversion of non-carbohydrate substances in the material. In this method, the biological conversion process can include fermentation.

Another embodiment of the present invention is a method for producing propanol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises propionic acid, a propionate ester, a propionate salt, or a mixture of propionic acid, propionate ester and a propionate salt, and wherein at least one intermediate is produced by a thermochemical conversion process and comprises hydrogen. In this method, the step of converting includes producing propionic acid, propionate ester propionate salt, or mixture of propionic acid, propionate ester and propionic salt by biological conversion of carbohydrate substances in the material and a portion of the hydrogen produced by the thermochemical conversion process. The method further includes chemically reacting remaining hydrogen and the propionic acid, propionate ester, propionate salt, or mixture of propionic acid, propionate ester and propionate salt to produce propanol. In this method, the chemical energy efficiency is greater than the chemical energy efficiency of a solely biological conversion process to produce propanol and is greater than the chemical energy efficiency of a process in which all of the material is initially subjected to a thermochemical conversion step as part of the process to produce propanol. In this method, the biological conversion process can include fermentation.

In another embodiment, the present invention includes a method for producing ethanol from a material comprising carbon-containing compounds, wherein less than about 75% by weight of the carbon-containing compounds are carbohydrate substances. This method includes converting the material into at least one intermediate, wherein the at least one intermediate is produced by a biological conversion process and comprises acetic acid, an acetate ester, an acetate salt, or a mixture of acetic acid, acetate ester and an acetate salt and a conversion process residue, and converting the conversion process residue into at least one intermediate, wherein the at least one intermediate is produced by a thermochemical conversion process and comprises a reductant. The method further includes chemically reacting the acetic acid, acetate salt, or mixture of acetic acid, acetate ester and acetate salt and the reductant to form ethanol. In this method, the chemical energy efficiency is greater than the chemical energy efficiency of a solely biological conversion process to produce ethanol and is greater than the chemical energy efficiency of a process in which all of the material is initially subjected to a thermochemical conversion step as part of the process to produce ethanol. In this method, the reductant can be selected from hydrogen, carbon monoxide, and a mixture of hydrogen and carbon monoxide. In addition, the step of converting can include producing at least a portion of the acetic acid, acetate ester, acetate salt, or mixture of acetic acid, acetate ester and acetate salt by a biological conversion process of carbohydrate substances in the material. In this method, the biological conversion process can include fermentation.

Another embodiment of the present invention is a method for producing ethanol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises a biological process-produced intermediate selected from the group consisting of acetic acid, an acetate ester, an acetate salt, or a mixture of acetic acid, acetate ester and acetate salt, and at least one intermediate is produced by a thermochemical conversion process and comprises hydrogen and methanol. In this method, the step of converting can include producing a portion of at least one biological process-produced intermediate by biological conversion of carbohydrate substances in the material, and producing a portion of at least one biological process-produced intermediate by biological conversion of methanol produced by the thermochemical process. The method further includes chemically reacting hydrogen produced by the thermochemical conversion process and biological process-produced intermediates to form ethanol. In this method, the chemical energy efficiency is greater than the chemical energy efficiency of a solely biological conversion process to produce ethanol and is greater than the chemical energy efficiency of a process in which all of the material is initially subjected to a thermochemical conversion step as part of the process to produce ethanol. In this method, the biological conversion process can include fermentation.

A further embodiment of the present invention is a method for producing butanol and ethanol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises butyric acid, a butyrate ester, a butyrate salt, acetic acid, an acetate ester, an acetate salt or a mixture thereof, and wherein at least one intermediate is produced by a thermochemical conversion process and comprises hydrogen. In this method, the step of converting can comprise producing butyric acid, butyrate ester, butyrate salt, acetic acid, acetate ester, acetate salt or mixture thereof by biological conversion of carbohydrate substances in the material and a portion of the hydrogen produced by the thermochemical conversion process. The method further includes chemically reacting remaining hydrogen and the butyric acid, butyrate ester, butyrate salt, acetic acid, acetate ester, acetate salt or mixture thereof to produce butanol and ethanol. In this method, the chemical energy efficiency is greater than the chemical energy efficiency of a solely biological conversion process to produce butanol and ethanol and is greater than the chemical energy efficiency of a process in which all of the material is initially subjected to a thermochemical conversion step as part of the process to produce butanol and ethanol. In this method, the biological conversion process can include fermentation.

A still further embodiment of the present invention is a method for producing 1,4-butanediol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises succinic acid, a succinate ester, a succinate salt, or a mixture of succinic acid, succinate ester and succinate salt, and wherein at least one intermediate is produced by a thermochemical conversion process and comprises a reductant. The method further includes chemically reacting the reductant and the succinic acid, succinate ester, succinate salt, or mixture of succinic acid, succinate ester and succinate salt to produce 1,4-butanediol. In this method, the chemical energy efficiency is greater than the chemical energy efficiency of a solely biological conversion process to produce 1,4-butanediol and is greater than the chemical energy efficiency of a process in which all of the material is initially subjected to a thermochemical conversion step as part of the process to produce 1,4-butanediol. Further, in this embodiment, the reductant can be selected from hydrogen, carbon monoxide, and a mixture of hydrogen and carbon monoxide. In this method, the step of converting can include producing the succinic acid, succinate ester, succinate salt, or mixture of succinic acid, succinate ester and succinate salt by a biological conversion process of carbohydrate substances in the material, and producing the reductant by a thermochemical conversion of non-carbohydrate substances in the material. In this method, the biological conversion process can include fermentation.

A still further embodiment of the present invention includes a method for producing 1,3-propanediol from a material comprising carbon-containing compounds, wherein less than about 75% by weight of the carbon-containing compounds are carbohydrate substances. This method includes converting the material into at least two intermediates, wherein at least one intermediate is produced by a biological conversion process and comprises 3-hydroxypropionic acid, a 3-hydroxypropionate ester, a 3-hydroxypropionate salt or a mixture of 3-hydroxypropionic acid, 3-hydroxypropionate ester and 3-hydroxypropionate salt, and wherein at least one intermediate is produced by a thermochemical conversion process and comprises a reductant. The method further includes chemically reacting the reductant and the 3-hydroxypropionic acid, 3-hydroxypropionate ester, 3-hydroxypropionate salt or mixture of 3-hydroxypropionic acid, 3-hydroxypropionate ester and 3-hydroxypropionate salt to produce 1,3-propanediol. In this method, the chemical energy efficiency is greater than the chemical energy efficiency of a solely biological conversion process to produce 1,3-propanediol and is greater than the chemical energy efficiency of a process in which all of the material is initially subjected to a thermochemical conversion step as part of the process to produce 1,3-propanediol. In this embodiment, the reductant can be selected from hydrogen, carbon monoxide, and a mixture of hydrogen and carbon monoxide. In addition, the step of converting can include producing the 3-hydroxypropionic acid, 3-hydroxypropionate ester, 3-hydroxypropionate salt or mixture of 3-hydroxypropionic acid, 3-hydroxypropionate ester and 3-hydroxypropionate salt by a biological conversion process of carbohydrate substances in the material, and producing the reductant by a thermochemical conversion of non-carbohydrate substances in the material. In this method, the biological conversion process can include fermentation.

DETAILED DESCRIPTION OF THE INVENTION

Figure 1:
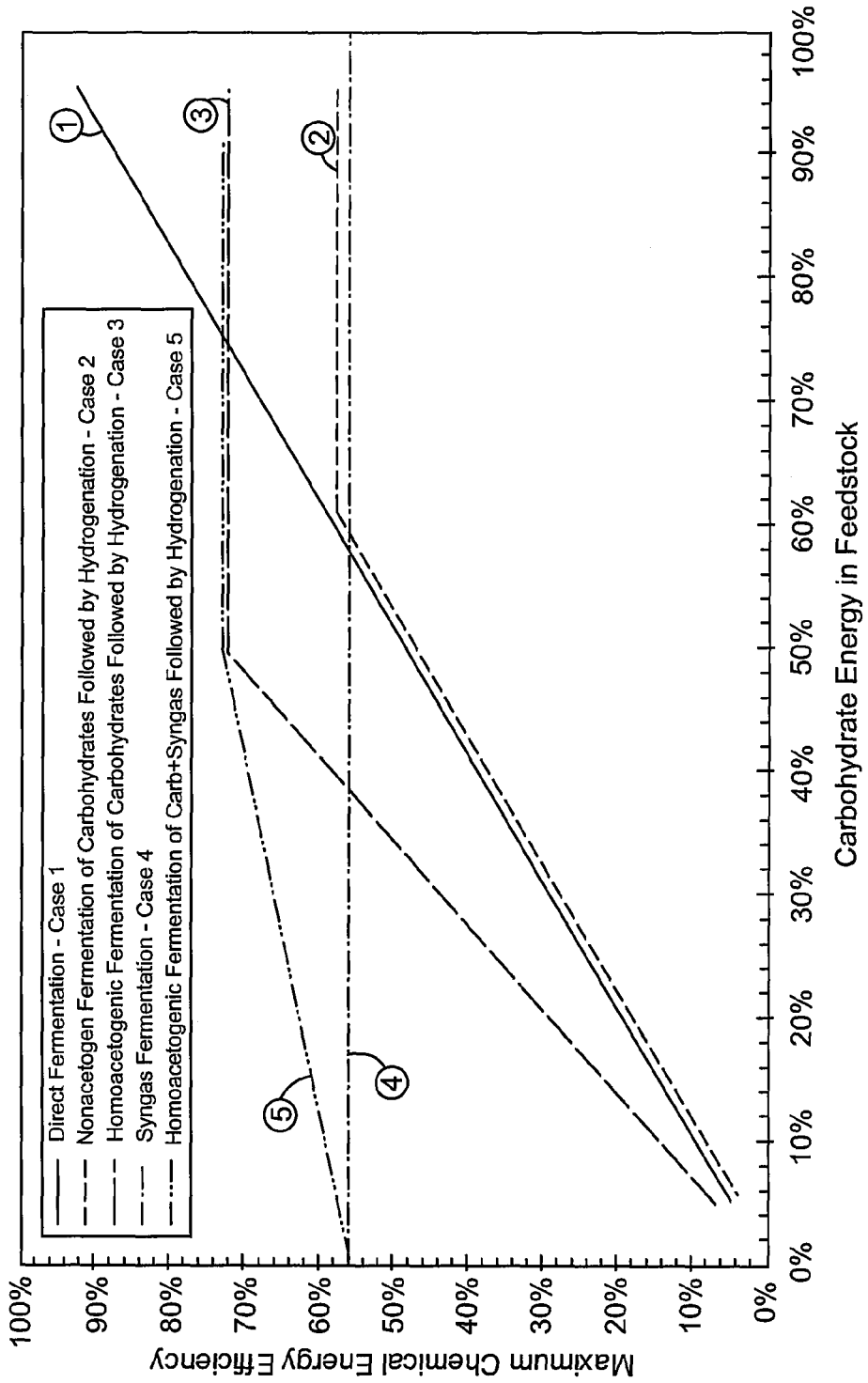
FIG. 1 illustrates the effect of biomass composition on the maximum theoretical energy conversion to ethanol for different conversion technologies.

The inventors have discovered a new method that overcomes limitations of the traditional routes to convert complex biomass to products. This method captures more of the energy, carbon and mass stored in all portions of the biomass and transfers that energy, carbon and mass to the products. The method comprises utilizing both biological and thermochemical conversion processes to produce intermediates. The intermediates produced by the two processes are then recombined in various ways into the desired product. This two-step or indirect method has important advantages in terms of energy and mass efficiency.

In one embodiment, the invention applies to complex biomass materials which are not pure sugars but which contain all of the fractions of biomass. The invention provides a method to convert such complex biomass to a desired product in which the efficiency of energy, carbon and mass transfer is higher than in any known process using complex biomass to produce such a desired product.

One embodiment of the invention is a method to produce a product from a material that includes carbon-containing compounds. The method includes the steps of (a) converting the material into at least two intermediates, such that at least one intermediate is produced by a biological conversion process and at least one intermediate is produced by a thermochemical conversion process, and (b) reacting at least one biological process-produced intermediate and at least one thermochemical process-produced intermediate to form the product. The chemical energy efficiency of the method of the present invention is greater than the chemical energy efficiency of a solely biological conversion process to produce the product and is greater than the chemical energy efficiency of a process in which all of the material is initially subjected to a thermochemical conversion step as part of the process to produce the product. The carbon-containing compounds in the material comprise less than 75% by weight carbohydrate substances.

The invention can include a process in which carbohydrate substances in the carbon-containing material are fermented into at least one biological process-produced intermediate and in which non-carbohydrate-containing materials are gasified to produce at least one thermochemical process-produced intermediate, such as syngas, a portion of which is fermented into at least one biological process-produced intermediate. The respective biological process-produced intermediates and at least one thermochemical process-produced intermediate are reacted to produce the desired product.

The invention includes a highly energy-efficient process that combines fermentation with gasification and subsequent reaction to produce chemicals and fuels from renewable resources. In such processes, both sugars and syngas components (CO, $H_2$, $CO_2$) in the fermentation medium are converted into organic acid intermediates. Using a combination of sugar and syngas components as feedstocks in a fermentation allows for high energy yield since all components of a typical biomass feedstock can be considered "fermentable". Both pure culture and mixed cultures of anaerobic bacteria can be used, depending upon the desired products. The resulting organic acid intermediates can either be recovered and used as is, or further processed into other useful chemicals and fuels such as aldehydes, esters, alcohols or alkenes.

A typical biomass resource contains cellulose, hemicellulose, and lignin plus lesser amounts of proteins, extractables, ash, etc. The complex carbohydrates contained in the cellulose and hemicellulose fractions can be processed into fermentable sugars using pretreatment and hydrolysis. When metabolized by anaerobic bacteria, these sugars can be converted into useful organic acid intermediates at both high energy and carbon yield. For example, when a homoacetogen is used to convert glucose into acetate,

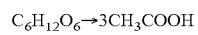

$$C_6H_{12}O_6 \rightarrow 3CH_3COOH$$

the reaction has 100% carbon yield and the resulting acetate contains about 94% of the chemical energy of the initial glucose. For purposes of discussion herein, the effects of cell mass production are ignored. Chemical energy efficiency is defined as the ratio of the heat of combustion of the products divided by the heat of combustion of the feeds, times 100 to convert into a percentage. For example, taking values from Table 3.7 of Roels, J. A., Energetics and Kinetics in Biotechnology, Elsevier Biomedical, 1983, the heat of combustion (HHV basis) of glucose and acetic acid are 2807 KJ/mol and 876 kJ/mol, respectively, so the chemical energy efficiency for this reaction is 3*876/2807*100=93.4%.

A typical biomass resource may have only about 60% of its chemical energy stored in the form of complex carbohydrates. The balance of the chemical energy stored in the biomass is in what is typically considered to be non-fermentable forms like lignin.

Many anaerobic bacteria are capable of fermenting syngas components (CO, $H_2$, $CO_2$ mixtures) into useful products. Table 1 shows that many homoacetogens will produce acetate from syngas mixtures at about 77% chemical efficiency. Another class of anaerobic bacteria, known as heteroacetogens, can produce ethanol directly from syngas mixtures at chemical energy efficiencies of about 80%. The literature has many more examples of anaerobic bacteria capable of metabolizing both sugar and syngas feedstocks. For example, the *Acetonema* and *Eubacterium* (*Butyribacterium*) will produce mixtures of acetate and butyric acids from these feedstocks.

TABLE 1

Examples of chemical energy efficiencies of homoacetogens and heteroacetogens

| | Chemical Energy Efficiency, % |
|---|---|
| Homoacetogens | |
| $4CO + 2H_2O \rightarrow CH_3COOH + 2CO_2$ | 77.4 |
| $2CO + 2H_2 \rightarrow CH_3COOH$ | 77.0 |
| $2CO_2 + 4H_2 \rightarrow CH_3COOH + 2H_2O$ | 76.6 |
| Heteroacetogens - Ethanol as Major Product | |
| $6CO + 3H_2O \rightarrow CH_3CH_2OH + 4CO_2$ | 80.6 |
| $2CO + 4H_2 \rightarrow CH_3CH_2OH + H_2O$ | 80.1 |
| $2CO_2 + 6H_2 \rightarrow CH_3CH_2OH + 3H_2O$ | 79.8 |

(computations based on values in Roels, J. A., Energetics and Kinetics in Biotechnology, Elsevier Biomedical, 1983)

The consortium of bacteria in a natural anaerobic environment will produce a variety of organic acid intermediates from the fermentable fractions of the organic matter in biomass feedstocks. The typical products from such a fermentation are acetate, propionate, butyrate, hydrogen, carbon dioxide, and methane. A pure culture of homoacetogens can be used to drive most of the products to acetate. This acetate can then be recovered as an organic salt or organic acid, or further transformed into an aldehyde, ester, alcohol or alkene. The resulting organic acid mixture can be recovered and/or transformed into organic acid salts, acids, aldehydes, esters, alcohols, alkenes. If desired, the mixtures can be separated into relatively pure fractions.

The invention includes the use of both the sugar and syngas metabolic pathways in acetogens and other bacteria to drive the carbon and chemical energy of the feed into acetate and other organic acid intermediates. Anaerobic fermentations of sugars are typically very efficient from a chemical energy point of view. Such fermentations are, however, limited by the amount of energy present in the feedstock in either a sugar or complex carbohydrate form. Syngas fermentations are typically inefficient from a chemical energy point of view. The chemical energy efficiency for gasification (a.k.a. cold gas efficiency) for biomass gasification is typically around 70%, and the chemical efficiency of syngas fermentation is about 77% to about 80%. In series, the two steps provide a theoretical maximum chemical energy yield of about 56%. However, an advantage of syngas fermentation is that all organic fractions of the feedstock can contribute both carbon and chemical energy to the final product.

One advantage of feeding both sugars and syngas to the fermentation is that this removes any restrictions on the maximum obtainable energy efficiency caused by limitations in the amount of carbon present in the feedstock in the form of fermentable and/or complex carbohydrates. This is especially useful for biomass feedstock with relatively low levels of energy in the form of carbohydrates.

With reference to FIG. 1, calculations showing the maximum theoretical chemical energy yield of ethanol as a function of biomass feedstock for several competing technologies are illustrated. The calculations are based on simplifying assumptions such as all of the carbohydrate energy is in the form of glucose, all reactions are driven to 100% completion, a gasifier cold gas efficiency of 70%, 85% chemical energy efficiency for recovery of $H_2$ from the syngas, no net import or export of power or steam, and all power and steam needed to run the process can be generated from waste heat. Each case will be discussed in more detail below.

Case 1 is the direct fermentation of a starting material. The yield of ethanol is directly proportional to the amount of carbohydrate present in the feed. This case is always carbohydrate carbon limited and produces high maximum theoretical yields only when the feedstock has very high carbohydrate content.

Case 2 is the non-acetogenic fermentation of carbohydrates to acetate followed by hydrogenation to produce ethanol. In this case, two moles of acetate are produced per mole of glucose fermented. For feedstock carbohydrate energy levels below about 60%, there is enough residual energy in the non-carbohydrate fraction to provide the hydrogen needed for hydrogenation. In this case, the system is carbohydrate carbon limited and the net production is two moles of ethanol per mole of glucose in the feed, the same as direct fermentation. At feedstock carbohydrate levels above about 60%, there is not enough energy in the non-carbohydrate fraction to provide the hydrogen needed for hydrogenation unless some of the carbohydrate is gasified as well. In this case, the system is energy limited and the overall chemical energy efficiency is about 58%.

Case 3 is the homoacetogenic fermentation of carbohydrates to acetate followed by hydrogenation to produce ethanol. As in Case 2, the system can either be carbohydrate carbon limited or energy limited. The break point occurs at about 50% for the assumptions used in the calculations. This case always has a higher maximum theoretical yield compared to Case 2. The maximum theoretical yield is also higher when compared to Case 1 for feedstocks containing less than about 75% of their energy in the form of carbohydrates. Case 3 exemplifies many of the embodiments disclosed herein.

Case 4 is the gasification of an entire feedstock followed by heteroacetogenic fermentation of syngas to produce ethanol. The maximum chemical energy efficiency of this case is independent of feedstock composition. Under the assumptions of the calculations, Case 4 has a higher maximum energy efficiency than Cases 1, 2, and 3 when the feedstock contains relatively low levels of energy in the form of carbohydrate.

Case 5 is the homoacetogenic fermentation of carbohydrates and syngas followed by hydrogenation to produce ethanol. As in Cases 2 and 3, the maximum chemical energy efficiency is divided into two regions. The system is energy limited for feedstocks with carbohydrate carbon energy contents above about 50%, meaning that some of the carbohydrate would have to be gasified to produce hydrogen for the hydrogenation step. The system is carbon limited for feed carbohydrate energy levels below 50%. However, since carbon can be supplied in the form of both syngas and carbohydrate, the fall off in maximum chemical energy efficiency is not as dramatic as in Cases 2 and 3. This case, which also exemplifies some embodiments of the present invention, has the highest maximum chemical energy efficiency except in high carbohydrate feedstocks, where the direct fermentation case has the advantage.

Most biomass resources have about 60% of their energy tied-up in the form of carbohydrates, so the technologies of Cases 3 and 5 are preferred for obtaining the highest possible maximum chemical energy efficiency. Case 5 outperforms Case 3 at low carbohydrate energy levels. Low carbohydrate energy levels can refer to actual levels, for instance woody materials with lots of bark, or it can refer to "effectively" low levels, for instance softwoods are particularly recalcitrant to pretreatment and enzymatic hydrolysis where their effective carbohydrate energy content is lower than implied from the chemical composition.

As referenced above, the present inventions are directed to methods for the conversion of materials that include carbon-containing compounds at high energy efficiencies. As discussed above with reference to FIG. 1, the energy efficiency of conversion of starting materials by direct fermentation is proportional to the amount of carbohydrate present in the starting material. Thus, high energy efficiencies can be achieved by direct fermentation of materials having high carbohydrate contents. For example, for materials having more than about 75% by weight of the carbon-containing compound as carbohydrates, a solely biological conversion process, such as direct fermentation of the material, to produce ethanol, for example, is the most efficient method of conversion of the methods depicted in FIG. 1. In comparison, the energy efficiency of a conversion of an entire feedstock of starting materials by a thermochemical process, such as by gasification, followed by a fermentation to produce ethanol, for example, is independent of the feedstock composition and is about 56%. Inventions disclosed herein, in contrast, include methods to convert a material comprising less than about 75% by weight carbohydrate substances into a product in a manner such that the chemical energy efficiency of the inventive methods to produce the product from the material is greater than the chemical energy efficiency of a solely biological conversion process to produce the product and is greater than the chemical energy efficiency of a conversion process in which all of the material is initially subjected to a thermochemical conversion step as part of the process to produce the product. It is to be appreciated that the composition and amount of material in each of the methods, or processes, described in the previous sentence is the same.

One present invention is a method for producing a product from a material that includes carbon-containing compounds. Such materials are characterized by having less than about 75% by weight of the carbon-containing compounds as carbohydrate substances. The method includes converting the material into at least two intermediates. At least one of the intermediates is produced by a biological conversion process and at least one of the intermediates is produced by a thermochemical conversion process. The method further includes reacting at least one intermediate produced by a biological process with at least one intermediate produced by a thermochemical process to form the product. In this invention, the chemical energy efficiency of the method to produce the product is greater than the chemical energy efficiency of a conversion process that is solely a biological conversion process to produce the product and is greater than the chemical energy efficiency of a conversion process in which all of the material is first subjected to a thermochemical conversion step as part of the process to produce the product. As used herein, terms such as "converting," "reacting," "producing," and the like are to be understood as referring to partial, as well as complete, processes. For example, reference to "reacting an intermediate", "reacting the intermediate", "reacting the intermediates", "reacting the remaining intermediate" and "reacting at least one intermediate" shall be construed to encompass both "reacting all of the at least one intermediate" and "reacting only a portion of the at least one intermediate," unless one or the other of such interpretations is specified. This understanding of such terms applies not only to the general term intermediate, but to all specific intermediates, such as reductant, acetic acid, etc.

The present inventions include a material comprising carbon-containing compounds. Such a material includes both carbohydrate substances and non-carbohydrate substances. As used herein, the term carbohydrate substance refers to the class of organic compounds that comprise one or more monosaccharide units. Unmodified monosaccharide units have the general formula $C_m(H_2O)_m$, where m represents the number of carbons in the monosaccharide unit; typically m is at least 3. Unmodified and/or modified monosaccharides can be linked in a variety of ways to form more complex carbohydrates. A material of the present invention comprises less than about 75% by weight carbohydrate. Methods to determine carbohydrate content are known to those skilled in the art.

Non-carbohydrate substances can include proteins, lipids, nucleic acids and a variety of chemical compounds. Non-carbohydrate substances typically found in materials of the present invention include lignin, proteins, resinous materials and minerals.

In some embodiments, the material comprising carbon-containing compounds can be biomass. In some embodiments, the material comprising carbon-containing compounds can be selected from herbaceous matter, agricultural residue, forestry residue, municipal solid waste, waste paper, pulp and paper mill residue. In some embodiments, the material containing carbon-containing compounds can be selected from trees, shrubs, grass, wheat, wheat straw, wheat midlings, sugar cane bagasse, corn, corn husks, corn kernel, corn fiber, municipal solid waste, waste paper, yard waste, branches, bushes, energy props, fruits, fruit peals, flowers, grains, herbaceous crops, leaves, bark, needles, logs, roots, saplings, short rotation woody crops, switch grasses, vegetables, vines, sugar beet pulp, oak hulls, hard woods, wood chips, intermediate streams from pulping operations, such as sulfite liquor, and soft woods. In particular embodiments, the material comprising carbon-containing compounds can be selected from trees, grasses, whole plants, and structural components of plants.

The term biological conversion process refers to a process in which the chemical nature of a material comprising carbon-containing compounds is changed by a biological process. For example, such a biological conversion process can include a fermentation process or an enzymatic process.

In some embodiments, the biological conversion process comprises a fermentation process such as a process that comprises culturing at least one microorganism in a liquid medium. Such a microorganism can be an aerobe or an anaerobe. In preferred embodiments of the present inventions, the fermentation is conducted with anaerobic bacteria. Suitable microorganisms include wild-type microorganisms, recombinant microorganisms or microorganisms that have been the subject of traditional strain development efforts. Fermentations of the present inventions can include either pure cultures of a single microorganism or mixed cultures of two or more microorganisms. Such mixed cultures can either be defined such that the mixture is purposefully created by combining two or more pure cultures or they can be a consortium of microorganisms from a natural environment. In some embodiments, the microorganism is a homofermentative microorganism. In some embodiments, the microorganism is not a homofermentative microorganism. As used herein, the term homofermentative refers to microorganism, that when cultured, produces a single, or substantially single, end product. For example, suitable microorganisms include homoacetogenic microorganisms, homolactic microorganisms, propionic acid bacteria, butyric acid bacteria, succinic acid bacteria, and 3-hydroxypropionic acid bacteria. More particularly, in preferred embodiments, the microorganism can be of a genus selected from the group *Clostridium, Lactobacillus, Moorella, Thermoanaerobacter, Proprionibacterium, Propionispera, Anaerobiospirillum,* and *Bacteriodes*. In still further, preferred embodiments, the microorganism can be of a species selected from *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus,* and *Bacteriodes ruminicola*. In one embodiment, a recombinant microorganism engineered to produce a desired product, such as a recombinant *Escherichia coli* transformed with one or more genes capable of encoding proteins that direct the production of the desired product is used; see, for example, U.S. Pat. No. 6,852,517, issued Feb. 8, 2005.

Process conditions, media and equipment suitable for fermentation of microorganisms of the present inventions are known in the art and can be selected based on the microorganism being used.

The term intermediate refers to a compound that is produced in accordance with embodiments of the present inventions and is then converted to at least one other compound in accordance with embodiments of the present inventions. In various embodiments of the present inventions, intermediates produced by a biological conversion process (biological process-produced intermediates) comprise a carboxylic acid, a salt thereof, or a mixture thereof. More particularly, an intermediate produced by a biological process can be selected from acetic acid, lactic acid, propionic acid, butyric acid, succinic acid, and 3-hydroxypropionic acid, a salt of any of the acids, and a mixture of any of the acids and respective salts. In some embodiments, an intermediate produced by a biological process can be selected from acetic acid, an acetate salt, a mixture of acetic acid and acetate salt, lactic acid, a lactate salt, a mixture of lactic acid and lactate salt, propionic acid, a propionate salt, a mixture of propionic acid and propionate salt, butyric acid, a butyrate salt, a mixture of butyric acid and butyrate salt, succinic acid, a succinate salt, and a mixture of succinic acid and succinate salt, 3-hydroxypropionic acid, a 3-hydroxypropionate salt, and a mixture of 3-hydroxypropionic acid and 3-hydroxypropionate salt.

In various embodiments of present inventions, an acid or acid salt intermediate produced by a biological process can be treated by acidification and/or esterification prior to the step of reacting with a thermochemical process-produced intermediate. For example, an intermediate produced by a biological process can comprise a salt of a carboxylic acid in which case the method can further include acidifying the carboxylic acid salt to form a biological process-produced intermediate comprising a carboxylic acid. Biological process-produced intermediates comprising carboxylic acid can be esterified to form biological process-produced intermediates comprising carboxylic acid esters. Such acidification and esterification processes can be accomplished by biological or chemical means. In one embodiment, the step of acidifying can include introducing carbon dioxide or an acid with a lower pKa than the carboxylic acid being acidified to a solution comprising the salt of the carboxylic acid. In another embodiment, the step of acidifying includes introducing a tertiary amine with carbon dioxide to form an acid/amine complex. This process can further include contacting the acid/amine complex with a water immiscible solvent to form an ester of the water immiscible solvent and the carboxylic acid. Methods of acidification and esterification are described in more detail in WO 2005/073161 published on Aug. 11, 2005 and in WO 00/53791 published on Sep. 14, 2000, both of which are incorporated herein by reference in their entirety.

In various embodiments of the present inventions, biological process-produced intermediates comprise carboxylic acid esters, such as those produced by processes described above. Such esters can be any type of ester suitable for subsequent formation of products as described herein. For example, such esters can be alkyl esters. In some embodiments, such an intermediate can be selected from an acetate ester, a lactate ester, a propionate ester, a butyrate ester, a succinate ester, a 3-hydroxypropionate ester and a mixture thereof. Also included are intermediates comprising mixtures of such esters and their respective acids and/or salts.

As used herein, the term thermochemical conversion process refers to a process in which the chemical nature of a material comprising carbon-containing compounds is changed by process conditions including application of elevated temperatures. More particularly, a thermochemical conversion process can be selected from gasification, pyrolysis, reforming, and partial oxidation.

A gasification process converts a carbon-containing material into a synthesis gas (syngas) comprising carbon monoxide, carbon dioxide and hydrogen. Gasification of carbonaceous material for the recovery of energy and chemicals is a well-established technology and any suitable gasification process can be used. There are a number of process designs for biomass gasification. For example, in staged steam reformation with a fluidized-bed reactor, the biomass is first pyrolyzed in the absence of oxygen, then the pyrolysis vapors are reformed to synthesis gas with steam providing added hydrogen and oxygen. Process heat comes from burning the char. With a screw auger reactor, moisture (and oxygen) is introduced at the pyrolysis stage and process heat comes from burning some of the gas produced in the latter stage. In entrained flow reformation, both external steam and air are introduced in a single-stage gasification reactor. Partial oxidation gasification uses pure oxygen, with no steam, to provide the proper amount of oxygen.

In various embodiments of the present inventions, an intermediate produced by a thermochemical process (a thermochemical process-produced intermediate) can include syngas, a component of syngas, a mixture of syngas components, pyrolysis gas, a component of pyrolysis gas, or a mixture of pyrolysis gas components. In preferred embodiments, an intermediate produced by a thermochemical process can include hydrogen, carbon monoxide, carbon dioxide, methanol, or mixtures thereof.

In various embodiments of the present inventions, the step of reacting an intermediate produced by a biological process and an intermediate produced by a thermochemical process can comprise chemical conversion or biological conversion. Methods to react such intermediates are known to those skilled in the art. In some preferred embodiments, the step of reacting includes chemically reacting the intermediate produced by a biological process and intermediate produced by a thermochemical process. In such embodiments, the step of reacting the intermediates can include reduction to produce the product. Reduction, for example, can be hydrogenation, hydrogenolysis or reduction by carbon monoxide. In some embodiments, reacting the products by a biological process can include the use of enzymatic treatment, immobilized cells (such as disclosed in U.S. Pat. No. 4,851,344).

Products produced by the step of reacting include organic products, examples of which include an alcohol, a carboxylic acid, a salt of a carboxylic acid, and an ester of a carboxylic acid. In some embodiments, the product can be selected from a monohydric alcohol and a dihydric alcohol. In particular embodiments, the product can be selected from ethanol, propanol, propylene glycol, butanol, 1,4-butanediol, 1,3-propanediol, and methyl esters thereof. The present invention also includes further reacting any such primary products (e.g., ethanol, propanol, propylene glycol, butanol, 1,4-butanediol, 1,3-propanediol or methyl esters thereof) to form secondary products such as aldehydes, ketones, acrylic acid, methyl methacrylate, or ethylene by known processes.

The present inventions comprise methods to produce a product from a carbon-containing material in which the chemical energy efficiency of such production is greater than the chemical energy efficiency of either a solely biological conversion process to produce the product or a process in which all of the material is initially subjected to a thermochemical conversion step as part of the process to produce the product, each of these methods, or processes, using the same material. As used herein, the term chemical energy efficiency refers to the ratio of the higher heating value (HHV) of the starting materials to the HHV of the products times 100%. The term HHV refers to the gross calorific value or the gross energy of a substance. This term equals the amount of heat released by a specified quantity of a substance (initially at 25° C.) once that substance is combusted and the products have returned to a temperature of 25° C. As such, HHV takes into account the latent heat of vaporization of water in the combustion products. In various embodiments of the inventions, the chemical energy efficiency can be at least about 60%, at least about 65%, at least about 70%, at least about 75%, at least about 80% or about 82%. Preferably, a high percentage of the carbon in the material comprising carbon-containing compounds is converted into the product. Such percentages typically correlate strongly with chemical energy efficiencies.

In preferred embodiments of the present inventions, a high percentage of carbohydrate substances in the material comprising carbon-containing compounds is converted into the product. More particularly, at least about 70%, at least about 75%, at least about 80%, at least about 85%, at least about 90%, at least about 95% or about 100% of carbohydrate substances in the material comprising carbon-containing compounds is converted into the product. In one embodiment, more than 70% of carbohydrate substances in the material is converted into the product.

In some embodiments of the present inventions, essentially no carbon dioxide is produced by the biological conversion process. In other embodiments, only one mole of carbon dioxide is produced per mole of monosaccharide or monosaccharide unit in the starting material. Carbon dioxide can be measured using techniques known to those skilled in the art.

In various embodiments of the present inventions, the methods can also include a step of fractionating material comprising carbon-containing compounds. Such fractionating processes can form a carbohydrate-containing fraction and a non-carbohydrate-containing fraction, typically including lignin. It should be noted that reference to a carbohydrate-containing fraction and a non-carbohydrate-containing fraction refers to fractions in which the carbohydrate content or the non-carbohydrate (e.g., lignin) content of the fraction is enriched as compared to the carbohydrate or non-carbohydrate (e.g., lignin) content of the original starting material. Thus, such terms should not be construed to imply that, for example, either a carbohydrate-containing fraction contains no lignin or that a lignin-containing fraction contains no carbohydrate. In some such embodiments, the carbohydrate-containing fraction is converted into an intermediate by a biological conversion process and/or a non-carbohydrate (e.g., lignin)-containing fraction is converted to an intermediate by a thermochemical conversion process. The step of fractionating can be selected from physical treatment, metal ion treatment, ultra violet light treatment, ozone treatment, oxygen treatment, organosolv treatment, steam explosion treatment, lime impregnation with steam explosion treatment, lime impregnation without steam treatment, hydrogen peroxide treatment, hydrogen peroxide/ozone (peroxone) treatment, acid treatment, dilute acid treatment and base treatment.

In various embodiments, fractionation of material comprising carbon-containing compounds can include steps of pretreatment (e.g., softening biomass) and saccharification (e.g., generating sugars by acid hydrolysis or enzymatic treatment). Any suitable pretreatment process may be used for the purposes of this invention, and includes chemical, physical or biological means. The term "pretreatment" as used herein refers to any step intended to alter native biomass so that it can be more efficiently and economically converted to an intermediate product. Pretreatment methods can utilize acids of varying concentrations (including sulfuric acids, hydrochloric acids, organic acids, etc.) and/or other components such as ammonia, ammonium, lime, and the like. Pretreatment methods can additionally or alternatively utilize hydrothermal treatments including water, heat, steam or pressurized steam. Physical treatments, such as grinding, boiling, freezing, milling, vacuum infiltration, and the like may be used with the methods of the invention. The biomass may also be contacted with a metal ion, ultraviolet light, ozone, and the like. Additional pretreatment processes are known to those skilled in the art, and can include, for example, organosolv treatment, steam explosion treatment, lime impregnation with steam explosion treatment, hydrogen peroxide treatment, hydrogen peroxide/ozone (peroxone) treatment, dilute acid treatment, and base treatment, including ammonia fiber explosion (AFEX) technology. Two or more pretreatment processes may be used.

Many suitable pretreatment processes are known in the art. As an example, before biomass with high cellulosic content can be successfully treated with cellulase enzyme complex, the hemicelluloses are hydrolyzed with acid to release the cellulose from lignin, and thus open the cellulosic structure to action by the cellulase enzyme complex. The acid is subsequently neutralized prior to the enzymatic reactions.

Pretreatment can occur or be deployed in various types of containers, reactors, pipes, flow through cells and the like. Some pretreatment methods will cause hydrolysis of hemicellulose to pentose sugars, thereby at least initiating saccharification. Conventional pretreatment methods with acids alone also do not typically hydrolyze cellulose, although partial hydrolysis of cellulose may occur under some known pretreatment technologies.

After pretreatment, it is important to produce fermentable sugars from the pretreated material. For example, starch that is present in the pretreated material can be hydrolyzed to sugars, such as by acid hydrolysis which is known in the art. In addition, enzymes that provide fermentable sugars in biomass are known in the art and are contemplated for saccharification. For example, glucoamylase can be used to complete the hydrolysis of the starch molecule. Glucoamylase is an exoenzyme that attacks the ends of the starch molecule. The enzyme hydrolyzes both 1,4 and 1,6 linkages, so nearly complete hydrolysis of the starch can be achieved. Optimal conditions for glucoamylase are typically 58-62° C., pH 4.4-5.0, and 24-48 hours of residence time. Longer residence times are typically not beneficial since the enzyme also catalyzes the formation of non-fermentable disaccharides-processes called reversion and retrogradation.

Since many sources of biomass contemplated for use in the present invention do not contain large amounts of starch, it is desirable to utilize the other major carbohydrate fractions, including the hemicellulose and cellulose fractions.

Hydrolysis of hemicellulose can be carried out in several ways. Much research is known on acid hydrolysis, and enzymatic hydrolysis is also well known. Complete enzymatic hydrolysis of hemicellulose requires a mixture of enzymes. The pendant arabinose and glucuronic acids are removed from the xylose backbone using α-L-arabinofuranosidase and α-glucuronidase. The xylose backbone is hydrolyzed using endo-β-1,4-xylanase and β-xylosidase.

Several methods are known for the hydrolysis of cellulose to fermentable sugars. Much research is known on acid hydrolysis, and enzymatic hydrolysis is also well known. For example, cellulose is hydrolyzed by the synergistic action of three cellulase enzymes: endo-β-glucanase, exo-β-glucanase, and β-glucosidase. The endo-β-glucanase is an endoenzyme which randomly hydrolyzes the 1,4 linkages in the interior of the cellulose molecule. Exo-β-glucanase removes cellobiose units (a disaccharide of β-linked glucose) from the non-reducing end of the cellulose chain. β-glucosidase hydrolyzes a cellobiose unit into two glucose molecules. Working together, the three enzymes can convert cellulose into glucose monomer.

The hemicellulose and cellulose enzymes have been the focus of much research work over the past 10-20 years. These enzymes are required for efficient conversion of woody biomass materials into fermentable sugars, which can then be used as fermentation feedstocks for ethanol and other fermentation products by traditional processes. Lignin degrading enzymes and other accessory enzymes such as ferulic esterases, can be used as well in processes of the present invention.

Reduction in enzyme cost can be obtained by overlapping the saccharification activity with the fermentation process in a design called Simultaneous Saccharification and Fermentation (SSF). Product inhibition of the cellulases is avoided by conversion of the glucose into ethanol or other desired fermentation product. The SSF philosophy has been used for decades by the ethanol industry with starch enzymes. This concept also works for the hemicellulase and cellulase enzyme systems. This process may also be used in the current invention. It is a desirable process because the fermentation used in this invention utilizes more of the types of sugars produced in the hydrolysis and further accelerates the hydrolysis compared to a yeast fermentation which consumes the glucose fraction largely. It is also a feature of this invention that certain bacteria, such as lactic acid bacteria and homoacetogens, as described in this invention utilize cellobiose directly, which also reduces feedback inhibition of the hydrolysis.

In addition to the utilization of the fiber fraction of starting materials comprising hemicellulose and cellulose, it may be desirable in this invention to utilize the protein fraction.

Protease enzymes are used to hydrolyze the proteins in starting materials into smaller peptides and amino acids. These amino acids and peptides are a major nitrogen source for the fermentation bacteria. Hydrolysis of the proteins speeds nitrogen assimilation in the fermentation. U.S. Pat. No. 4,771,001 shows the use of protease enzymes to increase the utilization of proteins by a lactic acid fermentation. This patent also illustrates the use of a different raw material, in this case cheese whey. For the purposes of the current invention the protein used to supplement the fermentation can come from the biomass, or from other protein sources and can be mixed into the media. Any protein source that produces a suitable fermentation media for the subsequent fermentation (including lactic acid or acetic acid fermentation) and does not inhibit the fermentation may be used.

As part of the fractionation process, the carbohydrates are separated from the lignin and other non-fermentable components to facilitate the remaining method steps. The separation can occur before, during or after additional pretreatment steps. For example, lignin can be removed in chemi-mechanical processes that free the cellulose for subsequent conversion to fermentable sugars. Lignin can also be removed by enzymatic methods, such as the use of ligninase. Often, two or more steps are employed in delignification.

One invention disclosed herein is a method for producing a product from a material that includes carbon-containing compounds wherein less than about 75% the weight of the carbon-containing compounds are carbohydrate substances. This process includes producing at least one intermediate by fermentation of carbohydrate substances in the material. This method further includes producing at least one intermediate by thermochemical conversion of non-carbohydrate substances in the material. This invention further includes chemically reacting these two intermediates to produce a product. In this process the chemical energy efficiency is greater than the chemical energy efficiency of either a solely biological conversion process and is greater than the chemical energy efficiency of a conversion process having thermochemical conversion of all of the starting materials.

A further invention disclosed herein is a method for producing a product from a material that includes carbon-containing compounds, wherein less than about 75% by weight of the carbon-containing compounds are carbohydrate substances. This process includes producing a portion of the at least one biological process-produced intermediate by fermentation of carbohydrate substances in the material. This process also includes producing at least one intermediate by thermochemical conversion of non-carbohydrate substances in the material that includes carbon-containing compounds. The method further includes producing a portion of the at least one biological process-produced intermediate by fermentation of a portion of the intermediate produced by thermochemical conversion of non-carbohydrate substances in the material. The process further includes chemically reacting the intermediate produced by fermentation with at least a portion of the remaining intermediate produced by chemical conversion of the non-carbohydrate substances in the material. In this process, the chemical energy efficiency of the method to produce a product from the material is greater than the chemical energy efficiency of either a solely biological conversion process or a conversion process having thermochemical conversion of all of the starting materials.

A still further invention disclosed herein is a method for producing a product from a material that includes carbon-containing compounds, wherein less than 75% by weight of the carbon-containing compounds are carbohydrate substances. This method includes fermenting the material to produce at least one biological process-produced intermediate and fermentation residue that includes non-fermented components of the material. The process further includes producing an intermediate by thermochemical conversion of the fermentation residue, and further includes chemically reacting the at least one biological process-produced intermediate and the intermediate produced by thermochemical conversion of the fermentation residue to produce the product.

Figure 2:
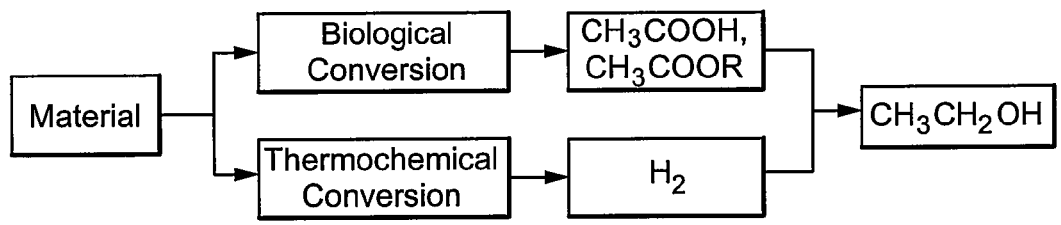
FIG. 2 illustrates a specific embodiment of the present invention for the production of ethanol.

With regard to the figures, various inventions disclosed herein are illustrated. With specific reference to FIG. 2, one invention is a method for producing ethanol from a material that includes carbon-containing compounds and wherein less than about 75% by weight of the carbon-containing compounds are carbohydrate substances. This invention includes converting the material into at least two intermediates. One intermediate is produced by a biological conversion process and comprises acetic acid, an acetate ester, an acetate salt, or a mixture of acetic acid, acetate ester and acetate salt. In FIG. 2 (as well as FIGS. 3-13), reference to the acid (e.g., $CH_3COOH$) should be understood to include both the acid as well as corresponding salts. In addition, reference to "a mixture of acetic acid, acetate ester and acetate salt" and other similar phrases refers to a mixture of any two or more of the listed components. Another intermediate is produced by a thermochemical conversion process and comprises a reductant. In this process, the reductant can be selected from hydrogen, carbon monoxide, and a mixture of hydrogen and carbon monoxide The method further includes chemically reacting the reductant and the acetic acid, acetate ester, acetate salt, or a mixture of acetic acid, acetate ester and acetate salt to produce ethanol. The chemical energy efficiency of this method to produce ethanol is greater than the chemical energy efficiency of either a solely biological conversion process or a conversion process in which all of the material is initially subjected to a thermochemical conversion step as part of the process to produce ethanol.

In a further embodiment of this invention, the step of converting can include producing at least a portion of the acetic acid, acetate ester, acetate salt, or a mixture thereof by a biological conversion process of carbohydrate substances in the material. Further, the step of converting can include producing at least a portion of the reductant by a thermochemical conversion process of non-carbohydrate substances in the material. In still further embodiments, the biological conversion process can include fermentation.

Figure 3:
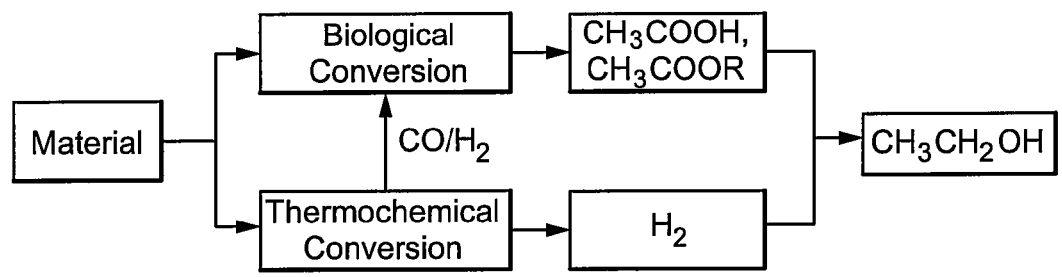
FIG. 3 illustrates a specific embodiment of the present invention for the production of ethanol.

With reference to FIG. 3, a further invention is illustrated. This is a method for producing ethanol from a material that includes carbon-containing compounds wherein less than about 75% by weight of the carbon-containing compounds are carbohydrate substances. The method includes converting the material into two intermediates. At least one intermediate is produced by a biological conversion process and includes a biological process-produced intermediate selected from acetic acid, an acetate ester and an acetate salt, or a mixture of acetic acid, acetate ester and acetate salt. The other intermediate is produced by a thermochemical conversion process and includes hydrogen and carbon monoxide. In the process, the step of converting includes producing a portion of at least one biological process-produced intermediate by biological conversion of carbohydrate substances in the material and producing a portion of at least one biological process-produced intermediate by biological conversion of carbon monoxide and a portion of the hydrogen produced by the thermochemical conversion process. The process further includes chemically reacting remaining hydrogen, and/or other reductants, produced by the thermochemical conversion process and the biological process-produced intermediates to produce ethanol. In this process, the chemical energy efficiency of the method to produce ethanol is greater than the chemical energy efficiency of either a solely biological conversion process or a conversion process in which all of the material is initially subjected to a thermochemical conversion step as part of the process to produce ethanol.

In further embodiments of this invention, the biological conversion process can include fermentation.

Figure 4:
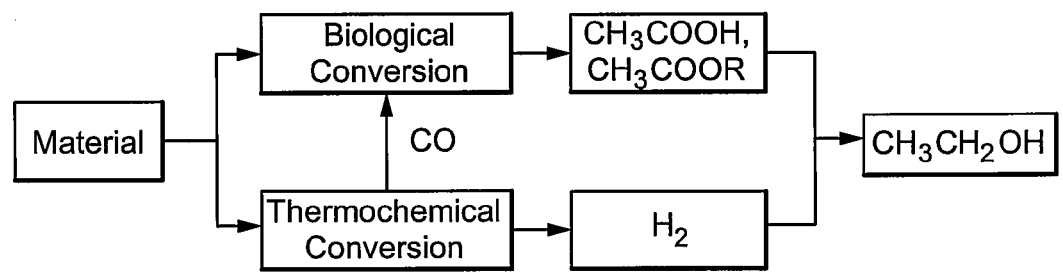
FIG. 4 illustrates a specific embodiment of the present invention for the production of ethanol.

With reference to FIG. 4, a further invention is illustrated. This invention is a method for producing ethanol from a material that includes carbon-containing compounds wherein less than about 75% by weight of the carbon-containing compounds are carbohydrate substances. This method includes converting the material into at least two intermediates. At least one intermediate is produced by a biological conversion process and includes a biological process-produced intermediate selected from acetic acid, an acetate ester, an acetate salt, or a mixture of acetic acid, acetate ester and acetate salt. At least one other intermediate is produced by a thermochemical conversion process and includes hydrogen and carbon monoxide. In this process, the step of converting includes producing a portion of at least one biological process-produced intermediate by biological conversion of carbohydrate substances in the material and producing a portion of at least one biological process-produced intermediate by biological conversion of a portion of the carbon monoxide produced by the thermochemical conversion process. The process further includes chemically reacting hydrogen, and/or other reductants, produced by the thermochemical conversion process and the biological process-produced intermediates to form ethanol. In this process, the chemical energy efficiency of the method to produce ethanol is greater than the chemical energy efficiency of either a solely biological conversion process to produce ethanol or a conversion process in which all of the material is initially subjected to a thermochemical conversion step as part of the process to produce ethanol.

In further embodiments of this invention, the biological conversion process can include fermentation.

Figure 5:
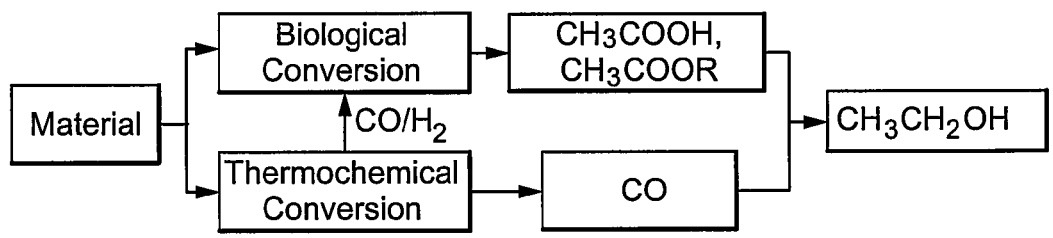
FIG. 5 illustrates a specific embodiment of the present invention for the production of ethanol.

With reference to FIG. 5, a further invention disclosed herein is illustrated. This invention is directed toward a method for producing ethanol from a material comprising carbon-containing compounds, wherein less than about 75% by weight of the carbon-containing are carbohydrate substances. The method includes converting the material into at least two intermediates, wherein at least one intermediate is produced by a biological conversion process and includes a biological process-produced intermediate selected from acetic acid, an acetate ester, an acetate salt, or a mixture thereof, and at least one intermediate is produced by a thermochemical conversion process and includes hydrogen and carbon monoxide. The step of converting includes producing a portion of at least one biological process-produced intermediate by biological conversion of carbohydrate substances in the material and producing a portion of at least one biological process-produced intermediate by biological conversion of a portion of the carbon monoxide and a portion of the hydrogen produced by the thermochemical conversion process. The method further includes chemically reacting remaining carbon monoxide, and/or other reductants, produced by the thermochemical conversion process and biological process-produced intermediates of steps (a) and (b) to form ethanol. In this process, the chemical energy efficiency of the method to produce ethanol from the material is greater than the chemical energy efficiency of a solely biological conversion process and is greater than the chemical energy efficiency of a process in which all of the material is initially subjected to a thermochemical conversion step as part of the process to produce ethanol.

In further embodiments of this invention, the biological conversion process can include fermentation and the thermochemical conversion process can include a chemical conversion process.

Figure 6:
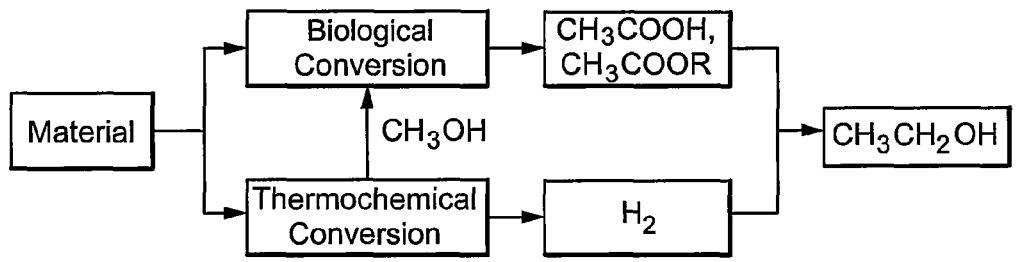
FIG. 6 illustrates a specific embodiment of the present invention for the production of ethanol.

A further invention disclosed herein is illustrated in FIG. 6. This invention is directed toward a method for producing ethanol from a material that includes carbon-containing compounds, wherein less than about 75% the weight of the carbon-containing compounds are carbohydrate substances. The method converting the material into at least two intermediates. At least one intermediate is produced by a biological conversion process and includes a biological process-produced intermediate selected from acetic acid, an acetate ester, an acetate salt, or mixtures thereof. At least one other intermediate is produced by a thermochemical conversion process and comprises hydrogen and methanol. In this process, the step of converting includes producing a portion of at least one biological process-produced intermediate by biological conversion of carbohydrate substances in the material and producing a portion of at least one biological process-produced intermediate by biological conversion of methanol produced by the thermochemical process. The process further includes chemically reacting hydrogen, and/or other reductants, produced by the thermochemical conversion process and biological process-produced intermediates to form ethanol. In this process, the chemical energy efficiency of the method is greater than the chemical energy efficiency of a solely biological conversion process or a conversion process in which all of the material is initially subjected to a thermochemical conversion step as part of the process to produce ethanol.

In further embodiments of this invention, the biological conversion process can include fermentation.

Figure 7:
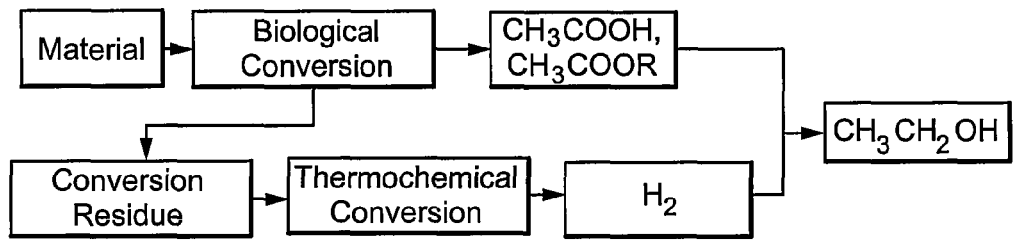
FIG. 7 illustrates a specific embodiment of the present invention for the production of ethanol.

With reference to FIG. 7, a further invention disclosed herein is illustrated. This invention includes a method for producing ethanol from a material that includes carbon-containing compounds, wherein less than about 75% by weight of the carbon-containing compounds are carbohydrate substances. This method includes converting material into at least one intermediate by a biological conversion process, wherein the intermediate comprises acetic acid, an acetate ester, an acetate salt, or mixtures thereof and a conversion process residue. The process further includes converting the conversion process residue into at least one intermediate that comprises a reductant by a thermochemical conversion process. In this process, the reductant can be selected from hydrogen, carbon monoxide, and a mixture of hydrogen and carbon monoxide. The process further includes chemically reacting the acetic acid, acetate ester, acetate salt or mixtures thereof with reductant to form ethanol. In this method, the chemical energy efficiency of the method is greater than the chemical energy efficiency of a solely biological conversion process to produce ethanol or a conversion process in which all of the material is initially subjected o a thermochemical conversion step as part of the process to produce ethanol.

In further embodiments of this invention, the step of converting can include producing at least a portion of the acetic acid, acetate ester, acetate salt or mixtures thereof by a biological conversion process of carbohydrate substances in the material. Further, the biological conversion process can include fermentation and the thermochemical conversion process can include a chemical conversion process.

Figure 8:
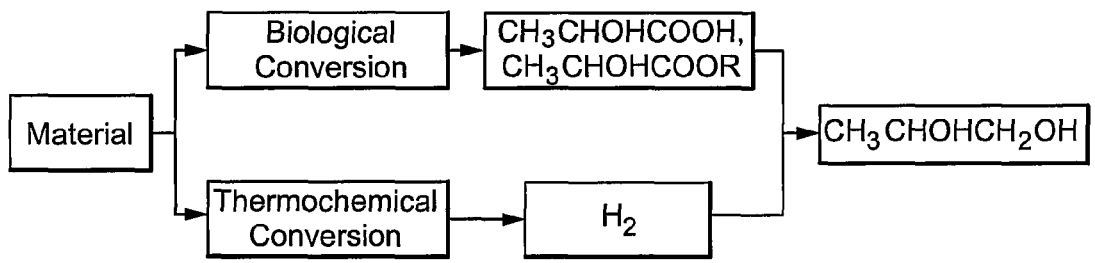
FIG. 8 illustrates a specific embodiment of the present invention for the production of propylene glycol.

With reference to FIG. 8, a further invention disclosed herein is illustrated. This invention is directed toward a method for producing propylene glycol from a material that includes carbon-containing compounds, wherein less than about 75% by weight of the carbon-containing compounds are carbohydrate substances. This method includes converting the material into at least two intermediates. One of the intermediates is produced by a biological conversion process and comprises lactic acid, a lactate ester, a lactate salt, or mixtures thereof. Another intermediate is produced by a thermochemical conversion process and includes a reductant. In this process, the reductant can be selected from hydrogen, carbon monoxide, and a mixture of hydrogen and carbon monoxide. The method further includes chemically reacting the reductant and the lactic acid, lactate ester, lactate salt, or mixture thereof to produce propylene glycol. In this method, the chemical energy efficiency of the method is greater than either the chemical energy efficiency of a solely biological conversion process to produce propylene glycol or a conversion process in which all of the material is initially subjected to a thermochemical conversion step as part of the process to produce propylene glycol.

In further embodiments of this invention, the step of converting can include producing the lactic acid, lactate ester, lactate salt, or a mixture thereof by a biological conversion process of carbohydrate substances in the material. Further, the step of converting can include producing the reductant by a thermochemical conversion process of non-carbohydrate substances in the material. In still further embodiments, the biological conversion process can include fermentation.

Figure 9:
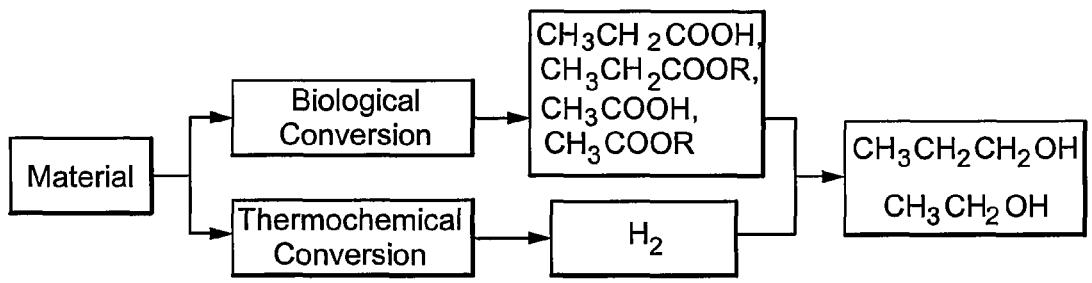
FIG. 9 illustrates a specific embodiment of the present invention for the production of propanol and ethanol.

With reference to FIG. 9, a further invention disclosed herein is illustrated. This invention is directed toward a method for producing propanol and ethanol from a material that includes carbon-containing compounds, wherein less than about 75% by weight of carbon-containing compounds are carbohydrate substances. This invention includes converting the material into at least two intermediates. At least one intermediate is produced by a biological conversion process and comprises propionic acid, a propionate ester, a propionate salt, acetic acid, an acetate ester, an acetate salt or a mixture thereof. At least one other intermediate is produced by a thermochemical conversion process and includes a reductant. In this process, the reductant can be selected from hydrogen, carbon monoxide, and a mixture of hydrogen and carbon monoxide. The process further includes chemically reacting the reductant and the propionic acid, propionate ester, propionate salt, acetic acid, acetate ester, acetate salt or a mixture thereof to produce propanol and ethanol. In this method, the chemical energy efficiency is greater than either the chemical energy efficiency of a solely biological conversion process to produce propanol and ethanol or a conversion process in which all of the material is initially subjected to a thermochemical conversion step as part of the process to produce propanol and ethanol.

In further embodiments of this invention, the step of converting can include producing the biological process-produced intermediate by a biological conversion process of carbohydrate substances in the material. Further, the step of converting can include producing the reductant by a thermochemical conversion process of non-carbohydrate substances in the material. In still further embodiments, the biological conversion process can include fermentation.

Figure 10:
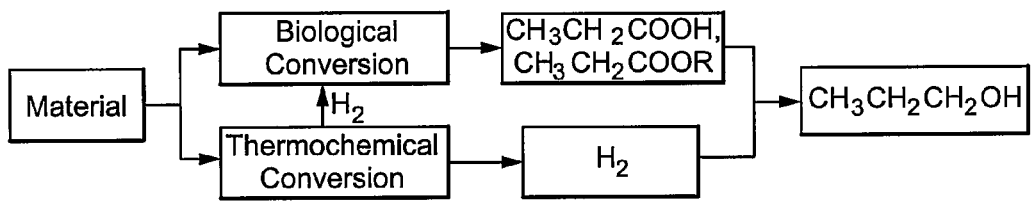
FIG. 10 illustrates a specific embodiment of the present invention for the production of propanol.

With reference to FIG. 10, a further invention disclosed herein is illustrated. This invention is directed toward a method for producing propanol from a material that includes carbon-containing compounds, wherein less than about 75% by weight of carbon-containing compounds are carbohydrate substances. This method includes converting the material into at least two intermediates, wherein at least one intermediate is produced by a biological conversion process and comprises propionic acid, a propionate ester, a propionate salt, or a mixture of propionic acid, propionate ester and propionate salt, and wherein at least one intermediate is produced by a thermochemical conversion process and comprises a reductant. In this process, the reductant can be selected from hydrogen, carbon monoxide, and a mixture of hydrogen and carbon monoxide. The step of converting comprises producing propionic acid, propionate ester, propionate salt, or mixture of propionic acid, propionate ester and propionate salt by biological conversion of carbohydrate substances in the material and a portion of the reductant produced by the thermochemical conversion process. The method further includes chemically reacting remaining hydrogen, and/or other reductants, and the propionic acid, propionate ester, propionate salt, or mixture of propionic acid, propionate ester and propionate salt to produce propanol. In this method, the chemical energy efficiency is greater than either the chemical energy efficiency of a solely biological conversion process to produce propanol or a conversion process in which all of the material is initially subjected to a thermochemical conversion step as part of the process to produce propanol. In still further embodiments, the biological conversion process can include fermentation.

Figure 11:
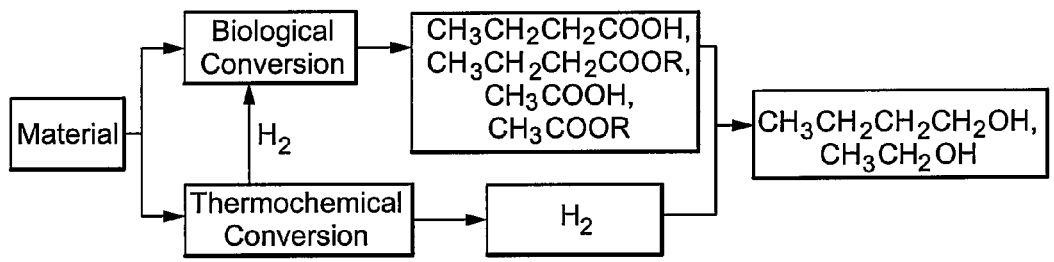
FIG. 11 illustrates a specific embodiment of the present invention for the production of butanol and ethanol.

With reference to FIG. 11, a further invention disclosed herein is illustrated. This invention is directed toward a method for producing butanol and ethanol from a material that includes carbon-containing compounds, wherein less than about 75% by weight of carbon-containing compounds are carbohydrate substances. This method includes converting the material into at least two intermediates, wherein at least one intermediate is produced by a biological conversion process and comprises butyric acid, a butyrate ester, a butyrate salt, acetic acid, an acetate ester, an acetate salt or a mixture of butyric acid, butyrate ester, butyrate salt, acetic acid, acetate ester and acetate salt and wherein at least one intermediate is produced by a thermochemical conversion process and comprises a reductant. In this process, the reductant can be selected from hydrogen, carbon monoxide, and a mixture of hydrogen and carbon monoxide. The step of converting comprises producing butyric acid, butyrate ester, butyrate salt, acetic acid, acetate ester, acetate salt or mixture of butyric acid, butyrate ester, butyrate salt acetic acid, acetate ester and acetate salt by biological conversion of carbohydrate substances in the material and a portion of the reductant produced by the thermochemical conversion process. The method further includes chemically reacting remaining hydrogen, and/or other reductants, and the butyric acid, butyrate ester, butyrate salt, acetic acid, acetate ester, acetate salt or mixture of butyric acid, butyrate ester, butyrate salt, acetic acid, acetate ester and acetate salt to produce butanol and ethanol. In this method, the chemical energy efficiency is greater than either the chemical energy efficiency of a solely biological conversion process to produce butanol and ethanol or a conversion process in which all of the material is initially subjected to a thermochemical conversion step as part of the process to produce butanol and ethanol. In still further embodiments, the biological conversion process can include fermentation.

Figure 12:
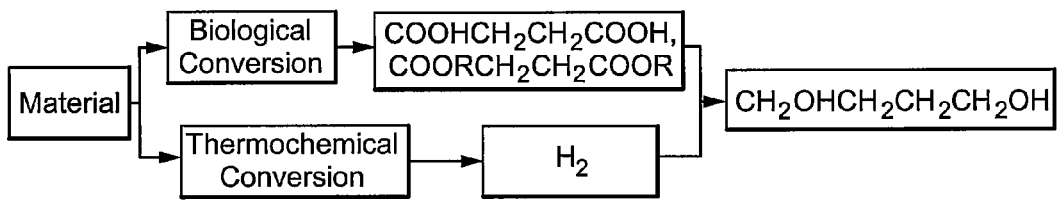
FIG. 12 illustrates a specific embodiment of the present invention for the production of 1,4-butanediol.

With reference to FIG. 12, a further invention disclosed herein is illustrated. This invention is directed toward a method for producing 1,4-butanediol from a material that includes carbon-containing compounds, wherein less than about 75% by weight of carbon-containing compounds are carbohydrate substances. This method includes converting the material into at least two intermediates, wherein at least one intermediate is produced by a biological conversion process and comprises succinic acid, a succinate ester, a succinate salt, or a mixture of succinic acid, succinate ester and succinate salt, and wherein at least one intermediate is produced by a thermochemical conversion process and comprises a reductant. In this process, the reductant can be selected from hydrogen, carbon monoxide, and a mixture of hydrogen and carbon monoxide. The method further includes chemically reacting reductant and the succinic acid, succinate ester, succinate salt, or mixture of succinic acid, succinate ester and succinate salt to produce 1,4-butanediol. In this method, the chemical energy efficiency is greater than either the chemical energy efficiency of a solely biological conversion process to produce 1,4-butanediol or a conversion process in which all of the material is initially subjected to a thermochemical conversion step as part of the process to produce 1,4-butanediol. In this method, the step of converting can comprise producing succinic acid, succinate ester, succinate salt, or mixture of succinic acid, succinate ester and succinate salt by biological conversion of carbohydrate substances in the material and producing the reductant by thermochemical conversion of non-carbohydrate substances in the material. In still further embodiments, the biological conversion process can include fermentation.

Figure 13:
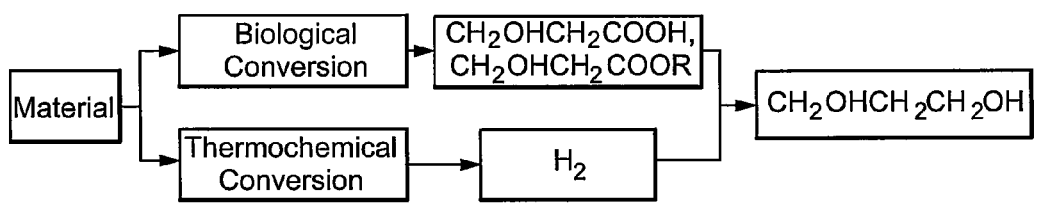
FIG. 13 illustrates a specific embodiment of the present invention for the production of 1,3-propanediol.

With reference to FIG. 13, a further invention disclosed herein is illustrated. This invention is directed toward a method for producing 1,3-propanediol from a material that includes carbon-containing compounds, wherein less than about 75% by weight of carbon-containing compounds are carbohydrate substances. This method includes converting the material into at least two intermediates, wherein at least one intermediate is produced by a biological conversion process and comprises 3-hydroxypropionic acid, 3-hydroxypropionate ester, 3-hydroxypropionate salt, or a mixture of 3-hydroxypropionic acid, 3-hydroxypropionate ester and 3-hydroxypropionate salt, and wherein at least one intermediate is produced by a thermochemical conversion process and comprises a reductant. In this process, the reductant can be selected from hydrogen, carbon monoxide, and a mixture of hydrogen and carbon monoxide. The method further includes chemically reacting the reductant and the 3-hydroxypropionic acid, 3-hydroxypropionate ester, 3-hydroxypropionate salt, or a mixture of 3-hydroxypropionic acid, 3-hydroxypropionate ester and 3-hydroxypropionate salt to produce 1,3-propanediol. In this method, the chemical energy efficiency is greater than either the chemical energy efficiency of a solely biological conversion process to produce 1,3-propanediol or a conversion process in which all of the material is initially subjected to a thermochemical conversion step as part of the process to produce 1,3-propanediol. In this method, the step of converting can comprise producing 3-hydroxypropionic acid, 3-hydroxypropionate ester, 3-hydroxypropionate salt, or a mixture of 3-hydroxypropionic acid, 3-hydroxypropionate ester and 3-hydroxypropionate salt by biological conversion of carbohydrate substances in the material and producing the reductant by thermochemical conversion of non-carbohydrate substances in the material. In still further embodiments, the biological conversion process can include fermentation.

The principles, preferred embodiments and modes of operation of the present invention have been described in the foregoing specification. The invention which is intended to be protected herein should not, however, be construed as limited to the particular forms disclosed, as these are to be regarded as illustrative rather than restrictive. Variations and changes may be made by those skilled in the art without departing from the spirit of the present invention. Accordingly, the foregoing best mode of carrying out the invention should be considered exemplary in nature and not as limiting to the scope and spirit of the invention as set forth in the appended claims.

What is claimed is:

1. A method for producing propanol and ethanol from a material, wherein the material comprises plant material or plant material that has been subject to pretreatment or saccharification, and wherein less than 75% by weight of the carbon-containing compounds in the material are carbohydrate substances, the method comprising:
   i) converting the material into at least a first intermediate and a second intermediate,
      wherein the first intermediate is produced by a biological conversion process and comprises propionic acid, a propionate ester, a propionate salt, acetic acid, an acetate ester, an acetate salt, or a mixture thereof, and
      wherein the second intermediate is produced by gasification and comprises a reductant; and
   ii) reacting the reductant and the propionic acid, propionate ester, propionate salt, acetic acid, acetate ester, acetate salt, or a mixture thereof by hydrogenation to produce propanol and ethanol,
   wherein the chemical energy efficiency of the method is greater than the chemical energy efficiency of i) a method in which the material is converted into propanol and ethanol using only a biological conversion process; and ii) a method in which all of the material is initially subjected to a thermochemical conversion step as part of the process to produce propanol and ethanol.

2. The method of claim 1, wherein said reductant is selected from the group consisting of hydrogen, carbon monoxide, and a mixture of hydrogen and carbon monoxide.

3. The method of claim 1, wherein the step of converting comprises
   (a) producing propionic acid, a propionate ester, a propionate salt, acetic acid, an acetate ester, an acetate salt, or a mixture thereof by a biological conversion process of carbohydrate substances in the material, and
   (b) producing the reductant by gasification of non-carbohydrate substances in the material.

4. The method of claim 1, wherein the biological conversion process comprises fermentation.

5. The method of claim 1, wherein the chemical energy efficiency of the method is at least 60%.

6. The method of claim 1, wherein the chemical energy efficiency of the method is at least 65%.

7. The method of claim 1, wherein the chemical energy efficiency of the method is at least 70%.

8. The method of claim 1, wherein the chemical energy efficiency of the method is at least 75%.

9. The method of claim 1, wherein the chemical energy efficiency of the method is at least 80%.

10. The method of claim 1, wherein the chemical energy efficiency of the method is 82%.

11. The method of claim 1, wherein at least 70% of carbohydrate substances in the material is converted into the product.

12. The method of claim 1, wherein greater than 70% of carbohydrate substances in the material is converted into the product.

13. The method of claim 1, wherein at least 75% of carbohydrate substances in the material is converted into the product.

14. The method of claim 1, wherein at least 80% of carbohydrate substances in the material is converted into the product.

15. The method of claim 1, wherein at least 90% of carbohydrate substances in the material is converted into the product.

16. The method of claim 1, wherein at least 95% of carbohydrate substances in the material is converted into the product.

17. The method of claim 1, wherein 100% of carbohydrate substances in the material is converted into the product.

18. The method of claim 1, wherein only one mole of carbon dioxide is produced per mole of monosaccharide or monosaccharide unit in the material.

19. The method of claim 1, wherein the plant material is selected from the group consisting of herbaceous matter, agricultural residue, forestry residue, municipal solid waste, waste paper, pulp and paper mill residue.

20. The method of claim 1, wherein the plant material is selected from the group consisting of trees, shrubs, grasses, wheat, wheat straw, wheat midlings, sugar cane bagasse, corn, corn husks, corn kernel, corn fiber, municipal solid waste, waste paper, yard waste, branches, bushes, energy crops, fruits, fruit peels, flowers, grains, herbaceous crops, leaves, bark, needles, logs, roots, saplings, short rotation woody crops, switch grasses, vegetables, vines, sugar beet pulp, oat hulls, hard woods, wood chips, intermediate streams from pulping operations and soft woods.

21. The method of claim 1, wherein the plant material is selected from the group consisting of trees, grasses, whole plants, and structural components of plants.

22. The method of claim 1, wherein the biological conversion process comprises fermentation.

23. The method of claim 1, wherein the biological conversion process comprises culturing at least one microorganism.

24. The method of claim 23, wherein the biological conversion process comprises culturing at least one homofermentative microorganism.

25. The method of claim 23, wherein the at least one microorganism is selected from the group consisting of homoacetogenic microorganisms, homolactic microorganisms, propionic acid bacteria, butyric acid bacteria, succinic acid bacteria and 3-hydroxypropionic acid bacteria.

26. The method of claim 23, wherein the at least one microorganism is of a genus selected from the group consisting of *Clostridium, Lactobacillus, Moorella, Thermoanaerobacter, Propionibacterium, Propionispera, Anaerobiospirillum,* and *Bacteriodes*.

27. The method of claim 23, wherein the at least one microorganism is of a species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*.

28. The method of claim 1, wherein the at least one thermochemical process-produced intermediate is selected from the group consisting of syngas, a component of syngas, a mixture of syngas components, pyrolysis gas, a component of pyrolysis gas, and a mixture of pyrolysis gas components.

29. The method of claim 1, wherein the at least one thermochemical process-produced intermediate is selected from the group consisting of hydrogen, carbon monoxide, carbon dioxide, and methanol.

30. The method of claim 1, wherein if the at least one biological process-produced intermediate comprises a salt of a carboxylic acid, the method further comprises acidifying the salt of the carboxylic acid to form the carboxylic acid prior to the step of reacting.

31. The method of claim 30, further comprising esterifying the carboxylic-acid prior to the step of reacting.

32. The method of claim 30, wherein the step of acidifying comprises introducing carbon dioxide, or an acid with a lower pKa than the carboxylic-acid of the intermediate being acidified, to a solution comprising the salt of the carboxylic acid.

33. The method of claim 30, wherein said step of acidifying comprises introducing a tertiary amine with carbon dioxide to form an acid/amine complex.

34. The method of claim 33, further comprising contacting the acid/amine complex with a water immiscible solvent to form an ester of the water immiscible solvent and the carboxylic acid.

35. The method of claim 1, wherein the step of reacting the at least one biological process-produced intermediate and the at least one thermochemical process-produced intermediate is a process of reduction to produce the product.

36. The method of claim 1, further comprising fractionating the material to form a carbohydrate-containing fraction, which is used to produce the first intermediate, and a residue fraction comprising lignin, which is used to produce the second intermediate.

37. The method of claim 36, wherein the step of fractionating is selected from the group consisting of physical treatment, metal ion treatment, ultraviolet light treatment, ozone treatment, oxygen treatment, organosolv treatment, steam explosion treatment, lime impregnation with steam explosion treatment, lime impregnation without steam treatment, hydrogen peroxide treatment, hydrogen peroxide/ozone (peroxone) treatment, acid treatment, dilute acid treatment, and base treatment.

38. The method of claim 1,
   (a) wherein the at least one biological process-produced intermediate is produced by fermentation of carbohydrate substances in the material,
   (b) wherein the at least one thermochemical process-produced intermediate is produced by thermochemical conversion of non-carbohydrate substances in the material, and
   (c) wherein the at least one biological process-produced intermediate of (a) and the at least one thermochemical process-produced intermediate of (b) are chemically reacted to produce the product.

39. The method of claim 1,
(a) wherein the material is fermented to produce at least one biological process-produced intermediate and a fermentation residue comprising non-fermented components of the material,
(b) wherein the at least one thermochemical process-produced intermediate is produced by thermochemical conversion of the fermentation residue, and
(c) wherein the at least one biological process-produced intermediate of (a) and the at least one thermochemical process-produced intermediate of (b) are chemically reacted to produce the product.

* * * * *